(12) United States Patent
Schorey et al.

(10) Patent No.: US 10,526,665 B2
(45) Date of Patent: Jan. 7, 2020

(54) EXOSOMAL BIOMARKERS DIAGNOSTIC OF TUBERCULOSIS

(71) Applicant: University of Notre Dame du Lac, South Bend, IN (US)

(72) Inventors: Jeffrey S. Schorey, Granger, IN (US); Prachi Pratap Singh, South Bend, IN (US); Yong Cheng, South Bend, IN (US)

(73) Assignee: University of Notre Dame du Lac, South Bend, IN (US)

( * ) Notice: Subject to any disclaimer, the term of this patent is extended or adjusted under 35 U.S.C. 154(b) by 154 days.

(21) Appl. No.: 15/449,324

(22) Filed: Mar. 3, 2017

(65) Prior Publication Data

US 2017/0253916 A1 Sep. 7, 2017

Related U.S. Application Data

(60) Provisional application No. 62/303,631, filed on Mar. 4, 2016.

(51) Int. Cl.
*C12Q 1/68* (2018.01)
*C12Q 1/689* (2018.01)

(52) U.S. Cl.
CPC ....... *C12Q 1/689* (2013.01); *C12Q 2600/158* (2013.01)

(58) Field of Classification Search
None
See application file for complete search history.

(56) References Cited

U.S. PATENT DOCUMENTS 9,255,924 B2 2/2016 Schorey et al.

FOREIGN PATENT DOCUMENTS

WO 2015164617 A1 10/2015

OTHER PUBLICATIONS

Handbook of Chemistry and Physics, 49th Edition, 1968, Weast (ed.), The Chemical Rubber Co., Cleveland, Ohio, p. A-245.*
Singh et al, Traffic 16: 555 (Mar. 5, 2015).*
Singh et al, J. Biomed. Sci. 20:14 (2013).*
Gallo, Alessia et al., "The Majority of Micrornas Detectable in Serum and Saliva Is Concentrated in Exosomes," PLoS One, Mar. 2012, vol. 7, Iss. 3, pp. 1-5.
Morin, Ryan D. et al., "Application of Massively Parallel Sequencing to Microrna Profiling and Discovery in Human Embryonic Stem Cells," Genome Research, 18:610-621 (2008).
Singh, Parchi P. et al., "Exosomes Released From M.Tuberculosis Infected Cells Can Suppress IFN-γ Mediated Activation of Naive Macrophages," PLoS One, Apr. 2011, vol. 6, Issue 4, pp. 1-10.
Sinha, Anirban et al., "Exosome-Enclosed Micrornas in Exhaled Breath Hold Potential for Biomarker Disclosvery in Patients With Pulmonary Diseases," Letters to the Editor, J. Allergy Clin. Immunol, Jul. 2013, vol. 132, No. 1, pp. 219-227e7.
Wang, Chuan et al., "Comparative Mirna Expression Profiles in Individuals With Latent and Active Tuberculosis," PLoS One, Oct. 2011, vol. 6, Issue 10, pp. 1-11.

* cited by examiner

*Primary Examiner* — James Martinell
(74) *Attorney, Agent, or Firm* — Haukaas Fortius PLLC; Michael H. Haukaas

(57) ABSTRACT

The disclosure provides a method for diagnosing an active *mycobacterium tuberculosis* infection by detecting certain RNA biomarkers present in secreted extracellular vesicles isolated from a bodily fluid. The RNA biomarkers in the secreted extracellular vesicles may include a certain mycobacterium RNAs as well as certain host cell RNAs. Also provided is an RNA signature of certain mycobacterium and host cell RNA present in secreted extracellular vesicles indicative of an active tuberculosis infection.

20 Claims, 25 Drawing Sheets

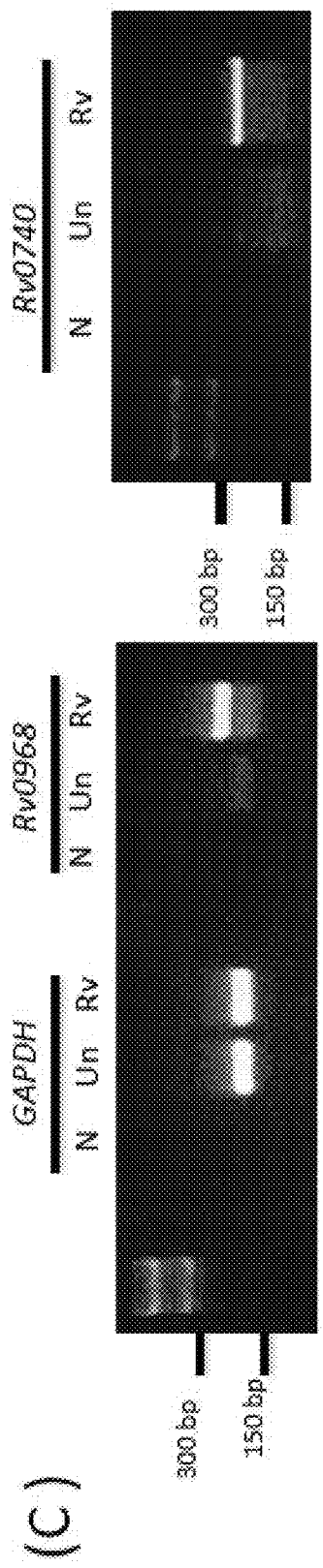

| Entry No. | Transcripts up/down | p value | X419442_2011.12.15_Cycle2_532_RV_exo.tif | X419442_2012.06.13_Cycle3_532_RV_exo.tif | X419442_2012.10.31_Area1_Cycle2_532_RV_exo.tif |
|---|---|---|---|---|---|
| 1. | XM_991975 | 0.008980266 | 14.69001831 | 15.27431981 | 14.9992978 |
| 2. | XM_988618 | 0.036933379 | 12.5638597 | 12.64730529 | 13.48558318 |
| 3. | XM_620069 | 0.011515922 | 12.90560679 | 12.75174025 | 13.21332416 |
| 4. | NM_001013815 | 0.016468505 | 13.64650921 | 13.91463049 | 14.61907371 |
| 5. | NM_130875 | 0.04300663 | 12.39152638 | 12.96829234 | 12.53025713 |
| 6. | XM_888908 | 0.012683696 | 15.03642859 | 14.32082763 | 14.8805453 |
| 7. | XM_972614 | 0.031033592 | 13.48024187 | 13.5665385 | 12.13223802 |
| 8. | NM_010385 | 0.008257258 | 12.71425848 | 11.98923182 | 13.22815893 |
| 9. | XM_892546 | 0.052795851 | 11.15021673 | 13.72727927 | 11.61888788 |
| 10. | XM_621565 | 0.027641511 | 13.30700067 | 13.70423215 | 14.11407425 |
| 11. | XM_991070 | 0.031180737 | 12.58639532 | 12.44924579 | 13.08919896 |
| 12. | NM_028782 | 0.021745606 | 10.94402732 | 12.20420683 | 12.07199622 |
| 13. | NM_008677 | 0.040185802 | 13.43155216 | 13.37267445 | 13.76557478 |
| 14. | XM_990951 | 0.021954121 | 13.2542231 | 13.66419337 | 12.87399735 |
| 15. | NM_023044 | 0.041741584 | 13.58654603 | 12.91288057 | 14.14408205 |
| 16. | XM_887617 | 0.014047229 | 11.05290531 | 12.01864503 | 11.58295143 |
| 17. | NM_010807 | 0.051554347 | 13.78649372 | 13.32770835 | 12.11075097 |
| 18. | NM_023596 | 0.025050243 | 12.62643244 | 12.32580724 | 12.37676037 |
| 19. | NM_198001 | 0.01638181 | 10.96936583 | 12.28038859 | 12.17821092 |
| 20. | NM_011809 | 0.003425234 | 11.02719369 | 10.191775 | 11.64910599 |
| 21. | XM_132434 | 0.049908833 | 13.04396579 | 13.79229278 | 13.68879833 |
| 22. | XM_979675 | 0.04666186 | 13.16655106 | 14.61511722 | 13.2840719 |
| 23. | XM_989063 | 0.006282218 | 14.61511722 | 15.09517604 | 15.52969971 |
| 24. | NM_025938 | 0.025268753 | 13.43781755 | 12.75018818 | 12.24711386 |
| 25. | XM_885366 | 0.044757172 | 12.21679992 | 13.18589371 | 13.38280354 |

*Fig. 11*

| Entry No. | X419442_2011.12.15_Cycle1_532_UN_exo.tif | X419442_2012.06.13_Cycle2_532_UN_exo.tif | X419442_2012.10.31_Area1_Cycle1_532_UN_exo.tif | diffm | FC |
|---|---|---|---|---|---|
| 1. | 12.43156256 | 11.72202994 | 11.50021459 | 3.099942944 | 8.573848615 |
| 2. | 11.37425865 | 9.500432189 | 9.709417683 | 2.704213217 | 6.517023587 |
| 3. | 11.0563271 | 9.751536871 | 10.05690021 | 2.668635676 | 6.358276149 |
| 4. | 12.25970075 | 11.50021459 | 11.89096925 | 2.176442941 | 4.520376507 |
| 5. | 11.58801896 | 10.0883193 | 9.746341781 | 2.158801934 | 4.45616278 |
| 6. | 13.72005999 | 12.18635582 | 12.53571226 | 1.931891182 | 3.815550396 |
| 7. | 12.154410666 | 10.69369863 | 10.66545637 | 1.888585574 | 3.7027203 |
| 8. | 10.44837892 | 10.55203758 | 11.41010365 | 1.840376358 | 3.581034351 |
| 9. | 10.03775497 | 10.62586193 | 10.3789985 | 1.817922826 | 3.525732025 |
| 10. | 12.40015 | 11.5474898 | 11.84796839 | 1.776566296 | 3.426097708 |
| 11. | 11.70036215 | 10.48725501 | 10.63317129 | 1.76801721 | 3.40585546 |
| 12. | 9.910618049 | 10.26713437 | 9.75858206 | 1.761298628 | 3.390031381 |
| 13. | 12.81335562 | 11.36825825 | 11.70831658 | 1.559990311 | 2.948518633 |
| 14. | 11.49389794 | 11.65598464 | 11.97775407 | 1.554925726 | 2.938185997 |
| 15. | 12.88724109 | 11.36979971 | 11.81674574 | 1.523240706 | 2.874359885 |
| 16. | 9.990233527 | 10.05374576 | 10.04564597 | 1.521625506 | 2.871143634 |
| 17. | 11.51524185 | 11.53354768 | 11.61409959 | 1.520687976 | 2.869278439 |
| 18. | 11.83215773 | 10.4798303 | 10.56164525 | 1.485122259 | 2.799408953 |
| 19. | 9.94953962 | 10.30822131 | 10.72175958 | 1.482781611 | 2.794870836 |
| 20. | 10.21148289 | 9.357719828 | | 1.479461646 | 2.788446606 |
| 21. | 12.57294362 | 11.89741031 | 11.62493447 | 1.476589497 | 2.782900826 |
| 22. | 12.35212865 | 12.28918316 | 12.19019731 | 1.411410351 | 2.659970693 |
| 23. | 13.29157352 | 13.914630049 | 13.91680962 | 1.405659777 | 2.649389169 |
| 24. | 12.71425848 | 11.06107727 | 10.58424914 | 1.358511569 | 2.564204935 |
| 25. | 11.582955143 | 11.05238312 | 12.09525939 | 1.351634409 | 2.552010755 |

*Fig. 11 (Cont.)*

| Entry No. | Description |
|---|---|
| 1. | XM_991975\|MM8\|transcript\|chr17\|35227512\|35231168\|ExemplarFor 'XM_991975'; gene_id '667708'; transcript_id 'XM_991975'; gene_name 'LOC667708'; alt '-'; hypothetical protein\|www.ncbi.nlm.nih.gov/entrez/query.fcgi?db=gene&cmd=Retrieve&dopt=full_report&list_uids=667708 |
| 2. | XM_620069\|MM8\|transcript\|chr4\|88250335\|88251891\|ExemplarFor 'XM_620069'; gene_id '545648'; transcript_id 'XM_620069'; gene_name 'LOC545648'; alt '-'; similar to interferon zeta\|www.ncbi.nlm.nih.gov/entrez/query.fcgi?db=gene&cmd=Retrieve&dopt=full_report&list_uids=545648 |
| 3. | NM_001013815\|MM8\|transcript\|chrX\|30562074\|30562559\|ExemplarFor 'NM_001013815'; gene_id '434448'; transcript_id 'NM_001013815'; gene_name 'RP23-230C18.1'; alt 'LOC434448'; similar to hypothetical protein MGC37588\|www.ncbi.nlm.nih.gov/entrez/query.fcgi?db=gene&cmd=Retrieve&dopt=full_report&list_uids=434448 |
| 4. | XM_888908\|MM8\|transcript\|chr2\|82224334\|82256671\|ExemplarFor 'XM_888908'; gene_id '624362'; transcript_id 'XM_888908'; gene_name 'LOC624362'; alt '-'; similar to HYPOTHETICAL PROTEIN ORF-1137\|www.ncbi.nlm.nih.gov/entrez/query.fcgi?db=gene&cmd=Retrieve&dopt=full_report&list_uids=624362 |
| 5. | XM_972614\|MM8\|transcript\|chr7\|59746213\|59759060\|ExemplarFor 'XM_972614'; gene_id '664788'; transcript_id 'XM_972614'; gene_name 'LOC664788'; alt '-'; hypothetical protein\|www.ncbi.nlm.nih.gov/entrez/query.fcgi?db=gene&cmd=Retrieve&dopt=full_report&list_uids=664788 |
| 6. | XM_892546\|MM8\|transcript\|chr7\|37585245\|37587039\|ExemplarFor 'XM_892546'; gene_id '627844'; transcript_id 'XM_892546'; gene_name 'LOC627844'; alt '-'; similar to Loricrin\|www.ncbi.nlm.nih.gov/entrez/query.fcgi?db=gene&cmd=Retrieve&dopt=full_report&list_uids=627844 |
| 7. | XM_991070\|MM8\|transcript\|chr1\|100419895\|100424966\|ExemplarFor 'XM_991070'; gene_id '666182'; transcript_id 'XM_991070'; gene_name 'LOC666182'; alt '-'; similar to putative retrovirus-related gag protein\|www.ncbi.nlm.nih.gov/entrez/query.fcgi?db=gene&cmd=Retrieve&dopt=full_report&list_uids=666182 |
| 8. | NM_028782\|MM8\|transcript\|chr17\|56299419\|56312007\|ExemplarFor 'NM_028782'; gene_id '74142'; transcript_id 'NM_028782'; gene_name 'Prss15'; alt '1200017E13Rik'\|LON'; protease, serine, 15\|www.ncbi.nlm.nih.gov/entrez/query.fcgi?db=gene&cmd=Retrieve&dopt=full_report&list_uids=74142 |
| 9. | NM_008677\|MM8\|transcript\|chr15\|78072088\|78089829\|ExemplarFor 'NM_008677'; gene_id '17972'; transcript_id 'NM_008677'; gene_name 'Ncf4'; alt 'AI451400\|p40phox'; neutrophil cytosolic factor 4\|www.ncbi.nlm.nih.gov/entrez/query.fcgi?db=gene&cmd=Retrieve&dopt=full_report&list_uids=17972 |

*Fig. 11 (Cont.)*

| Entry No. | Description |
|---|---|
| 10. | XM_990951|MM8|transcript|chr6|102140127|102143210|ExemplarFor 'XM_990951'; gene_name 'LOC666123'; alt ''; similar to CG33694-PA, isoform A|www.ncbi.nlm.nih.gov/entrez/query.fcgi?db=gene&cmd=Retrieve&dopt=full_report&list_uids=666123 |
| 11. | NM_023044|MM8|transcript|chr19|10909588|10924948|ExemplarFor 'NM_023044'; gene_id '65221'; transcript_id 'NM_023044'; gene_name 'Slc15a3'; alt 'Cl1|cl-1'; solute carrier family 15, member 3|www.ncbi.nlm.nih.gov/entrez/query.fcgi?db=gene&cmd=Retrieve&dopt=full_report&list_uids=65221 |
| 12. | XM_887617|MM8|transcript|chr9|98665864|98666704|ExemplarFor 'XM_887617'; gene_id '623186'; transcript_id 'XM_887617'; gene_name 'LOC623186'; alt ''; hypothetical LOC623186|www.ncbi.nlm.nih.gov/entrez/query.fcgi?db=gene&cmd=Retrieve&dopt=full_report&list_uids=623186 |
| 13. | NM_010807|MM8|transcript|chr4|129015947|129018279|ExemplarFor 'NM_010807'; gene_id '17357'; transcript_id 'NM_010807'; gene_name 'Marcksl1'; alt 'AL022768|AW215397|AW536807|D4Bc1|F52|MacMARCKS|Macs-2|Macs-3|Macs2|Macs3|Mlp|Mrp'; MARCKS-like 1|www.ncbi.nlm.nih.gov/entrez/query.fcgi?db=gene&cmd=Retrieve&dopt=full_report&list_uids=17357 |
| 14. | NM_023596|MM8|transcript|chr10|60107429|60148134|ExemplarFor 'NM_023596'; gene_id '71279'; transcript_id 'NM_023596'; gene_name 'Slc29a3'; alt '4933435C21Rik|AW987637|Ent3'; solute carrier family 29 (nucleoside transporters), member 3|www.ncbi.nlm.nih.gov/entrez/query.fcgi?db=gene&cmd=Retrieve&dopt=full_report&list_uids=71279 |
| 15. | XM_979675|MM8|transcript|chrX|127320034|127320343|ExemplarFor 'XM_979675'; gene_id '665817'; transcript_id 'XM_979675'; gene_name 'LOC665817'; alt ''; hypothetical protein LOC665817|www.ncbi.nlm.nih.gov/entrez/query.fcgi?db=gene&cmd=Retrieve&dopt=full_report&list_uids=665817 |
| 16. | XM_989063|MM8|transcript|chr11|48786430|48822804|ExemplarFor 'XM_989063'; gene_id '667214'; transcript_id 'XM_989063'; gene_name 'LOC667214'; alt ''; similar to immunity-related GTPase family, cinema 1|www.ncbi.nlm.nih.gov/entrez/query.fcgi?db=gene&cmd=Retrieve&dopt=full_report&list_uids=667214 |
| 17. | NM_026938|MM8|transcript|chr7|15611300|15614012|ExemplarFor 'NM_026938'; gene_id '69094'; transcript_id 'NM_026938'; gene_name '1810008O21Rik'; alt ''; RIKEN cDNA 1810008O21 gene|www.ncbi.nlm.nih.gov/entrez/query.fcgi?db=gene&cmd=Retrieve&dopt=full_report&list_uids=69094 |
| 18. | NM_024169|MM8|transcript|chr15|98552401|98556232|ExemplarFor 'NM_024169'; gene_id '66120'; transcript_id 'NM_024169'; gene_name 'Fkbp11'; alt '1110002O23Rik'; FK506 binding protein 11|www.ncbi.nlm.nih.gov/entrez/query.fcgi?db=gene&cmd=Retrieve&dopt=full_report&list_uids=66120 |

*Fig. 11 (Cont.)*

| Entry No. | Description |
|---|---|
| 19. | XM_001002539\|MM8\|transcript\|chr12\|20200427\|20200955\|ExemplarFor 'XM_001002539'; gene_id '668596'; transcript_id 'XM_001002539'; gene_name 'LOC668596'; alt '-'; hypothetical protein LOC668596\|www.ncbi.nlm.nih.gov/entrez/query.fcgi?db=gene&cmd=Retrieve&dopt=full_report&list_uids=668596 |
| 20. | NM_054042\|MM8\|transcript\|chr19\|5068077\|5070640\|ExemplarFor 'NM_054042'; gene_id '70445'; transcript_id 'NM_054042'; gene_name 'Cd248'; alt '2610111G01Rik\|AI842296\|Cd16411\|Tem1'; CD248 antigen, endosialin\|www.ncbi.nlm.nih.gov/entrez/query.fcgi?db=gene&cmd=Retrieve&dopt=full_report&list_uids=70445 |
| 21. | XM_901515\|MM8\|transcript\|chr8\|124239909\|124240431\|ExemplarFor 'XM_901515'; gene_id '629516'; transcript_id 'XM_901515'; gene_name 'LOC629516'; alt '-'; hypothetical LOC629516\|www.ncbi.nlm.nih.gov/entrez/query.fcgi?db=gene&cmd=Retrieve&dopt=full_report&list_uids=629516 |
| 22. | NM_009532\|MM8\|transcript\|chr7\|24255048\|24282192\|ExemplarFor 'NM_009532'; gene_id '22594'; transcript_id 'NM_009532'; gene_name 'Xrcc1'; alt 'MGC102556'; Xrcc-1'; X-ray repair complementing defective repair in Chinese hamster cells 1\|www.ncbi.nlm.nih.gov/entrez/query.fcgi?db=gene&cmd=Retrieve&dopt=full_report&list_uids=22594 |
| 23. | NM_011018\|MM8\|transcript\|chr11\|50043574\|50054213\|ExemplarFor 'NM_011018'; gene_id '18412'; transcript_id 'NM_011018'; gene_name 'Sqstm1'; alt 'A170\|OSF-6\|Osi\|STAP\|p62'; sequestosome 1\|www.ncbi.nlm.nih.gov/entrez/query.fcgi?db=gene&cmd=Retrieve&dopt=full_report&list_uids=18412 |
| 24. | NM_019738\|MM8\|transcript\|chr7\|126414393\|126416618\|ExemplarFor 'NM_019738'; gene_id '56312'; transcript_id 'NM_019738'; gene_name 'Nupr1'; alt '2310032H04Rik\|Com1\|p8'; nuclear protein 1\|www.ncbi.nlm.nih.gov/entrez/query.fcgi?db=gene&cmd=Retrieve&dopt=full_report&list_uids=56312 |
| 25. | XM_994682\|MM8\|transcript\|chr7\|28160434\|28161211\|ExemplarFor 'XM_994682'; gene_id '668161'; transcript_id 'XM_994682'; gene_name 'LOC668161'; alt '-'; hypothetical protein LOC668161\|www.ncbi.nlm.nih.gov/entrez/query.fcgi?db=gene&cmd=Retrieve&dopt=full_report&list_uids=668161 |

*Fig. 11 (Cont.)*

| Entry No. | Transcripts up/down | p value | X419442_2011.12.15_Cycle2_532_RV_exo.tif | X419442_2012.06.13_Cycle3_532_RV_exo.tif | X419442_2012.10.31_Area1_Cycle2_532_RV_exo.tif |
|---|---|---|---|---|---|
| 26. | NM_176848 | 0.024541686 | 11.4949445 | 11.74312292 | 11.91222832 |
| 27. | NM_024169 | 0.002938971 | 14.88820595 | 15.29180656 | 15.51216133 |
| 28. | XM_001002539 | 0.024652169 | 14.52652407 | 14.07929144 | 13.61360378 |
| 29. | NM_054042 | 0.031460725 | 12.06192883 | 11.8502602 | 12.25815981 |
| 30. | XM_901515 | 0.00564537 | 11.38434318 | 12.50014233 | 12.92396026 |
| 31. | XM_985034 | 0.052577843 | 12.76813519 | 12.41953037 | 12.7725688 |
| 32. | NM_023524 | 0.037455583 | 11.08356663 | 11.6412497 | 11.44456373 |
| 33. | NM_009532 | 0.012055332 | 12.10586091 | 13.26214174 | 12.86398922 |
| 34. | NM_007534 | 0.030375293 | 14.57131278 | 14.01782399 | 13.55060686 |
| 35. | NM_011018 | 0.031984238 | 11.0482261 | 11.71460739 | 13.1189776 |
| 36. | NM_019738 | 0.016564916 | 12.01718501 | 11.97261942 | 13.09841748 |
| 37. | XM_994682 | 0.049881696 | 12.68786423 | 13.34321325 | 13.16999678 |
| 38. | XM_357732 | 0.000209532 | 15.44324248 | 15.57738026 | 15.21559672 |
| 39. | NM_016852 | 0.037288388 | 13.91680962 | 14.03354524 | 14.11787562 |
| 40. | XM_889449 | 0.040992114 | 12.19329498 | 11.92867925 | 13.27632066 |
| 41. | NM_008556 | 0.000523393 | 12.9776402 | 13.24275466 | 12.94654083 |
| 42. | NM_194060 | 0.012776327 | 14.2050978 | 14.87391 | 14.55562104 |
| 43. | XM_001004127 | 0.020938508 | 11.10700289 | 10.67123915 | 11.08964217 |
| 44. | XM_901938 | 0.031406299 | 13.94614941 | 14.39215312 | 14.16327501 |
| 45. | XM_001000676 | 0.032546423 | 12.41953037 | 13.43403319 | 13.33922093 |
| 46. | XM_001004192 | 0.014781916 | 11.82949761 | 13.2307975 | 13.09315702 |
| 47. | XM_001003038 | 0.031881347 | 11.54207835 | 11.17838484 | 11.73033319 |
| 48. | NM_133954 | 0.01946641 | 11.27870593 | 12.46013624 | 12.55659665 |
| 49. | NM_007536 | 0.017722022 | 11.5532187 | 11.42143576 | 11.16667392 |
| 50. | NM_011063 | 0.042022402 | 12.63937424 | 13.42806454 | 14.39215312 |

*Fig. 11 (Cont.)*

| Entry No. | X419442_2011.12.15_Cycle1_532_UN_exo.tif | X419442_2012.06.13_Cycle2_532_UN_exo.tif | X419442_2012.10.31_Area1_Cycle1_532_UN_exo.tif | diffm | FC |
|---|---|---|---|---|---|
| 26. | 10.68249981 | 9.865010926 | 10.59072666 | 1.337352783 | 2.526872346 |
| 27. | 13.36131706 | 14.01782399 | 14.32680544 | 1.328742448 | 2.511836306 |
| 28. | 13.66822006 | 12.18281664 | 12.40360905 | 1.321591176 | 2.499416233 |
| 29. | 11.10087569 | 10.86676349 | 10.2428906 | 1.319939687 | 2.496556724 |
| 30. | 10.32555004 | 10.96018363 | 11.63350257 | 1.296403179 | 2.456157675 |
| 31. | 12.1591609 | 11.32274557 | 10.62950157 | 1.282942105 | 2.433347066 |
| 32. | 10.05153428 | 9.632898207 | 10.64890361 | 1.278681323 | 2.426171144 |
| 33. | 10.79575673 | 11.66726455 | 11.96093012 | 1.269346828 | 2.410524056 |
| 34. | 13.75366156 | 12.12064096 | 12.48046982 | 1.261657095 | 2.397709863 |
| 35. | 9.906875513 | 10.97379691 | 11.24014228 | 1.25366546 | 2.384464759 |
| 36. | 10.6495528 | 11.17288523 | 11.51677001 | 1.249671292 | 2.377872387 |
| 37. | 12.23492779 | 11.43258366 | 11.8025636 | 1.243666402 | 2.367995603 |
| 38. | 14.18496085 | 14.32680544 | 14.03639509 | 1.22935269 | 2.344617677 |
| 39. | 13.38280354 | 12.32413253 | 12.68302591 | 1.225089501 | 2.339320449 |
| 40. | 11.59261512 | 10.75127489 | 11.3833842 | 1.223673558 | 2.335406291 |
| 41. | 11.67533035 | 12.05852218 | 11.76376183 | 1.223107105 | 2.334489509 |
| 42. | 13.28109119 | 13.27632066 | 13.41859934 | 1.219539219 | 2.328723285 |
| 43. | 10.30432414 | 9.755349155 |  | 1.214937 | 2.321306459 |
| 44. | 13.21044451 | 12.57891029 | 13.08727134 | 1.208317137 | 2.310679454 |
| 45. | 11.8332844 | 11.76665943 | 12.05692461 | 1.17863868 | 2.263630811 |
| 46. | 10.9346627 | 11.65865133 | 12.05130655 | 1.169610513 | 2.249509583 |
| 47. | 10.4091776 | 10.54355453 | 10.03495442 | 1.154369945 | 2.225870941 |
| 48. | 10.59437685 | 11.08667546 | 11.15601741 | 1.152789698 | 2.223434181 |
| 49. | 10.83534765 | 10.19953989 | 9.70421581 | 1.134075011 | 2.194777987 |
| 50. | 12.17944828 | 12.13223802 | 12.75018818 | 1.132572476 | 2.192493363 |

*Fig. 11 (Cont.)*

| Entry No. | Description |
|---|---|
| 26. | XM_357732|MM8|transcript|chr7|32207490|32255562|ExemplarFor 'XM_357732'; gene_id '384591'; transcript_id 'XM_357732'; gene_name 'LOC384591'; alt '-'; similar to Glyceraldehyde-3-phosphate dehydrogenase (GAPDH)|www.ncbi.nlm.nih.gov/entrez/query.fcgi?db=gene&cmd=Retrieve&dopt=full_report&list_uids=384591 |
| 27. | XM_889449|MM8|transcript|chrX|116296098|116296359|ExemplarFor 'XM_889449'; gene_id '624906'; transcript_id 'XM_889449'; gene_name 'LOC624906'; alt '-'; similar to Ornithine decarboxylase (ODC)|www.ncbi.nlm.nih.gov/entrez/query.fcgi?db=gene&cmd=Retrieve&dopt=full_report&list_uids=624906 |
| 28. | NM_008556|MM8|transcript|chr1|174033402|174035090|ExemplarFor 'NM_008556'; gene_id 'N/A'; transcript_id 'NM_008556'; gene_name 'N/A'; alt 'N/A'; Mus musculus phosphoprotein enriched in astrocytes 15 (Pea15), transcript variant 1, mRNA.|www.ncbi.nlm.nih.gov/gquery/gquery.fcgi?term=NM_008556 |
| 29. | NM_194060|MM8|transcript|chr4|119764712|119784896|ExemplarFor 'NM_194060'; gene_id '329934'; transcript_id 'NM_194060'; gene_name 'Foxo6'; alt '-'; forkhead box O6|www.ncbi.nlm.nih.gov/entrez/query.fcgi?db=gene&cmd=Retrieve&dopt=full_report&list_uids=329934 |
| 30. | XM_001004127|MM8|transcript|chr17|88348695|88350132|ExemplarFor 'XM_001004127'; gene_id '668864'; transcript_id 'XM_001004127'; gene_name 'LOC668864'; alt '-'; hypothetical protein LOC668864|www.ncbi.nlm.nih.gov/entrez/query.fcgi?db=gene&cmd=Retrieve&dopt=full_report&list_uids=668864 |
| 31. | XM_001000676|MM8|transcript|chrX|97898816|97899581|ExemplarFor 'XM_001000676'; gene_id '668285'; transcript_id 'XM_001000676'; gene_name 'LOC668285'; alt '-'; hypothetical protein LOC668285|www.ncbi.nlm.nih.gov/entrez/query.fcgi?db=gene&cmd=Retrieve&dopt=full_report&list_uids=668285 |
| 32. | XM_001004192|MM8|transcript|chr2|120254865|120255378|ExemplarFor 'XM_001004192'; gene_id '668878'; transcript_id 'XM_001004192'; gene_name 'LOC668878'; alt '-'; hypothetical protein LOC668878|www.ncbi.nlm.nih.gov/entrez/query.fcgi?db=gene&cmd=Retrieve&dopt=full_report&list_uids=668878 |
| 33. | NM_133954|MM8|transcript|chr8|98221468|98236638|ExemplarFor 'NM_133954'; gene_id '101985'; transcript_id 'NM_133954'; gene_name 'AA960436'; alt '-'; expressed sequence AA960436|www.ncbi.nlm.nih.gov/entrez/query.fcgi?db=gene&cmd=Retrieve&dopt=full_report&list_uids=101985 |
| 34. | NM_011063|MM8|transcript|chr1|174033403|174043456|ExemplarFor 'NM_011063'; gene_id '18611'; transcript_id 'NM_011063'; gene_name 'Pea15'; alt 'Mat1|PEA-15|Pkcs15'; phosphoprotein enriched in astrocytes 15;www.ncbi.nlm.nih.gov/entrez/query.fcgi?db=gene&cmd=Retrieve&dopt=full_report&list_uids=18611 |

*Fig. 11 (Cont.)*

| Entry No. | Description |
|---|---|
| 35. | XM_974884|MM8|transcript|chr5|78340281|78340970|ExemplarFor 'XM_974884'; gene_id '665152'; transcript_id 'XM_974884'; gene_name 'LOC665152'; alt ''; hypothetical protein LOC665152|www.ncbi.nlm.nih.gov/entrez/query.fcgi?db=gene&cmd=Retrieve&dopt=full_report&list_uids=665152 |
| 36. | XM_973179|MM8|transcript|chr17|14191007|14191334|ExemplarFor 'XM_973179'; gene_id '664873'; transcript_id 'XM_973179'; gene_name 'LOC664873'; alt ''; hypothetical protein LOC664873|www.ncbi.nlm.nih.gov/entrez/query.fcgi?db=gene&cmd=Retrieve&dopt=full_report&list_uids=664873 |
| 37. | XM_982884|MM8|transcript|chr19|6044690|6044822|ExemplarFor 'XM_982884'; gene_id '666300'; transcript_id 'XM_982884'; gene_name 'LOC666300'; alt ''; similar to thymosin, beta 10|www.ncbi.nlm.nih.gov/entrez/query.fcgi?db=gene&cmd=Retrieve&dopt=full_report&list_uids=666300 |
| 38. | XM_976344|MM8|transcript|chr6|87423289|87423724|ExemplarFor 'XM_976344'; gene_id '665358'; transcript_id 'XM_976344'; gene_name 'LOC665358'; alt ''; hypothetical protein LOC665358|www.ncbi.nlm.nih.gov/entrez/query.fcgi?db=gene&cmd=Retrieve&dopt=full_report&list_uids=665358 |
| 39. | XM_887838|MM8|transcript|chr6|124263681|124263798|ExemplarFor 'XM_887838'; gene_id '623391'; transcript_id 'XM_887838'; gene_name 'LOC623391'; alt ''; similar to vacuolar H+ ATPase G1|www.ncbi.nlm.nih.gov/entrez/query.fcgi?db=gene&cmd=Retrieve&dopt=full_report&list_uids=623391 |
| 40. | XM_484341|MM8|transcript|chr14|6031824|6032830|ExemplarFor 'XM_484341,XM_889228'; gene_id '432817'; transcript_id 'XM_484341'; gene_name 'LOC432817'; alt ''; similar to esterase D/formylglutathione hydrolase|www.ncbi.nlm.nih.gov/entrez/query.fcgi?db=gene&cmd=Retrieve&dopt=full_report&list_uids=432817 |
| 41. | XM_985694|MM8|transcript|chr5|142613072|142613420|ExemplarFor 'XM_985694'; gene_id '666736'; transcript_id 'XM_985694'; gene_name 'LOC666736'; alt ''; hypothetical protein LOC666736|www.ncbi.nlm.nih.gov/entrez/query.fcgi?db=gene&cmd=Retrieve&dopt=full_report&list_uids=666736 |
| 42. | NM_012021|MM8|transcript|chr19|6973862|6976689|ExemplarFor 'NM_012021'; gene_id '54683'; transcript_id 'NM_012021'; gene_name 'Prdx5'; alt 'AOEB166|AOPP|Pmp20|Prdx6|PrxV'; peroxiredoxin 5|www.ncbi.nlm.nih.gov/entrez/query.fcgi?db=gene&cmd=Retrieve&dopt=full_report&list_uids=54683 |
| 43. | XM_130728|MM8|transcript|chr2|172163732|172165536|ExemplarFor 'XM_130728'; gene_id '76426'; transcript_id 'XM_130728'; gene_name '1700029J11Rik'; alt ''; RIKEN cDNA 1700029J11 gene|www.ncbi.nlm.nih.gov/entrez/query.fcgi?db=gene&cmd=Retrieve&dopt=full_report&list_uids=76426 |

*Fig. 11 (Cont.)*

| Entry No. | Description |
|---|---|
| 44. | NM_010787|MM8|transcript|chr17|46144327|46146296|ExemplarFor 'NM_010787'; gene_id '172256'; transcript_id 'NM_010787'; gene_name 'Mea1'; alt 'Mea-1'; male enhanced antigen 1;|www.ncbi.nlm.nih.gov/entrez/query.fcgi?db=gene&cmd=Retrieve&dopt=full_report&list_uids=17256 |
| 45. | XM_884867|MM8|transcript|chr7|84710543|84717877|ExemplarFor 'XM_884867'; gene_id '620480'; transcript_id 'XM_884867'; gene_name 'LOC620480'; alt '-'; similar to Eukaryotic translation initiation factor 1 (eIF1) (Protein translation factor SUI1 homolog) (Su-lisa1) (A121)|www.ncbi.nlm.nih.gov/entrez/query.fcgi?db=gene&cmd=Retrieve&dopt=full_report&list_uids=620480 |
| 46. | XM_989180|MM8|transcript|chr13|45974452|45975097|ExemplarFor 'XM_989180'; gene_id '667229'; transcript_id 'XM_989180'; gene_name 'LOC667229'; alt '-'; hypothetical protein LOC667229|www.ncbi.nlm.nih.gov/entrez/query.fcgi?db=gene&cmd=Retrieve&dopt=full_report&list_uids=667229 |
| 47. | NM_139219|MM8|transcript|chr8|23347280|23350966|ExemplarFor 'NM_139219'; gene_id '246079'; transcript_id 'NM_139219'; gene_name 'Defb9'; alt 'MGC129393'; defensin beta 9;|www.ncbi.nlm.nih.gov/entrez/query.fcgi?db=gene&cmd=Retrieve&dopt=full_report&list_uids=246079 |
| 48. | XM_980769|MM8|transcript|chr11|99596103|99596733|ExemplarFor 'XM_980769'; gene_id '665992'; transcript_id 'XM_980769'; gene_name 'LOC665992'; alt '-'; hypothetical protein LOC665992|www.ncbi.nlm.nih.gov/entrez/query.fcgi?db=gene&cmd=Retrieve&dopt=full_report&list_uids=665992 |
| 49. | XM_987621|MM8|transcript|chr16|32553907|32564642|ExemplarFor 'XM_987621'; gene_id '667001'; transcript_id 'XM_987621'; gene_name 'LOC667001'; alt '-'; hypothetical protein LOC667001|www.ncbi.nlm.nih.gov/entrez/query.fcgi?db=gene&cmd=Retrieve&dopt=full_report&list_uids=667001 |
| 50. | XM_993038|MM8|transcript|chr6|16939235|16939689|ExemplarFor 'XM_993038'; gene_id '667871'; transcript_id 'XM_993038'; gene_name 'LOC667871'; alt '-'; hypothetical protein LOC667871|www.ncbi.nlm.nih.gov/entrez/query.fcgi?db=gene&cmd=Retrieve&dopt=full_report&list_uids=667871 |

*Fig. 11 (Cont.)*

| Entry No. | Transcripts up/down | p value | X419442_2011.12.15_Cycle2_532_RV_exo.tif | X419442_2012.05.13_Cycle3_532_RV_exo.tif | X419442_2012.10.31_Area1_Cycle2_532_RV_exo.tif |
|---|---|---|---|---|---|
| 51. | XM_974884 | 0.035747647 | 12.17339036 | 11.64767728 | 12.10869703 |
| 52. | XM_973179 | 0.025524995 | 12.46013624 | 13.14616324 | 13.12158681 |
| 53. | XM_982884 | 0.012834136 | 13.24650363 | 13.42514348 | 13.95123689 |
| 54. | XM_976344 | 0.012568024 | 13.81307438 | 13.92338554 | 14.59391029 |
| 55. | XM_887838 | 0.030045608 | 11.27338009 | 12.04555281 | 11.89618355 |
| 56. | XM_484341 | 0.031136775 | 11.71460739 | 11.56444356 | 12.16076605 |
| 57. | XM_985694 | 0.018273456 | 13.63935751 | 13.74852392 | 14.07929144 |
| 58. | NM_012021 | 0.006282287 | 13.2840719 | 13.05536185 | 13.49626114 |
| 59. | NM_144554 | 0.028227983 | 12.42134245 | 12.01511289 | 12.38216492 |
| 60. | XM_130728 | 0.04972448 | 12.10499034 | 11.98105042 | 11.47757902 |
| 61. | NM_010907 | 0.047717736 | 12.13084442 | 11.89393274 | 10.92510499 |
| 62. | NM_010787 | 0.045710056 | 12.0403661 | 12.36608612 | 11.95062521 |
| 63. | NM_001017429 | 0.017795061 | 13.89707331 | 13.65851363 | 14.34392628 |
| 64. | NM_013585 | 0.001919334 | 11.5474898 | 12.87911647 | 12.6978863 |
| 65. | XM_884867 | 0.01977744 | 11.89840129 | 11.84875342 | 11.17514305 |

*Fig. 11 (Cont.)*

| Entry No. | X419442_2011.12.15_Cycle1_532_UN_exo.tif | X419442_2012.06.13_Cycle2_532_UN_exo.tif | X419442_2012.10.31_Area1_Cycle1_532_UN_exo.tif | diffm | FC |
|---|---|---|---|---|---|
| 51. | 11.03037167 | 11.07604495 | 10.42884759 | 1.131500151 | 2.190864335 |
| 52. | 10.82418049 | 12.39152638 | 12.13998814 | 1.124063761 | 2.179600552 |
| 53. | 12.45442402 | 12.27830185 | 12.5260565 | 1.121367212 | 2.175530453 |
| 54. | 12.97007977 | 12.8887711 | 13.14352289 | 1.109332153 | 2.157457519 |
| 55. | 9.960310485 | 10.59263047 | 11.35419663 | 1.102659623 | 2.147502221 |
| 56. | 11.17111175 | 10.3145271 | 10.6529187 | 1.100417896 | 2.144167922 |
| 57. | 12.93810541 | 12.62463804 | 12.63937424 | 1.088351726 | 2.126309675 |
| 58. | 12.3971323 | 11.99645378 | 12.18635582 | 1.085250997 | 2.121744587 |
| 59. | 11.794462985 | 10.97562878 | 10.83632492 | 1.070678902 | 2.10042155 |
| 60. | 11.5603695 | 10.21148289 | 10.5873214 | 1.068148666 | 2.096741004 |
| 61. | 11.64767728 | 10.21305256 | 9.9578362 | 1.043772036 | 2.061610851 |
| 62. | 11.67671257 | 10.94035812 | 10.6616611 | 1.026115211 | 2.036533027 |
| 63. | 12.86594318 | 12.98299634 | 12.98151874 | 1.023018322 | 2.032166094 |
| 64. | 10.56308971 | 11.73913062 | 11.76923115 | 1.017680361 | 2.024660987 |
| 65. | 11.12966136 | 10.43447169 | 10.34597647 | 1.004062751 | 2.005640107 |

*Fig. 11 (Cont.)*

| Entry No. | Description |
|---|---|
| 51. | XM_985693|MM8|transcript|chr5|65321300|65324338|ExemplarFor 'XM_985693'; gene_id '666735'; transcript_id 'XM_985693'; gene_name 'LOC666735'; alt '-'; similar to delangin isoform A|www.ncbi.nlm.nih.gov/entrez/query.fcgi?db=gene&cmd=Retrieve&dopt=full_report&list_uids=666735 |
| 52. | XM_974396|MM8|transcript|chr10|61075584|61076040|ExemplarFor 'XM_974396'; gene_id '665076'; transcript_id 'XM_974396'; gene_name 'LOC665076'; alt '-'; hypothetical protein LOC665076|www.ncbi.nlm.nih.gov/entrez/query.fcgi?db=gene&cmd=Retrieve&dopt=full_report&list_uids=665076 |
| 53. | XM_889112|MM8|transcript|chrX|145238479|145239547|ExemplarFor 'XM_889112'; gene_id '624568'; transcript_id 'XM_889112'; gene_name 'LOC624568'; alt '-'; hypothetical LOC624568|www.ncbi.nlm.nih.gov/entrez/query.fcgi?db=gene&cmd=Retrieve&dopt=full_report&list_uids=624568 |
| 54. | XM_990522|MM8|transcript|chr9|99542111|99609664|ExemplarFor 'XM_990522'; gene_id '667429'; transcript_id 'XM_990522'; gene_name 'LOC667429'; alt '-'; similar to IgE-binding protein|www.ncbi.nlm.nih.gov/entrez/query.fcgi?db=gene&cmd=Retrieve&dopt=full_report&list_uids=667429 |
| 55. | NM_001029877|MM8|transcript|chr7|18083870|18117322|ExemplarFor 'NM_001029877'; gene_id '384569'; transcript_id 'NM_001029877'; gene_name 'Nova2'; alt 'Gm1424'; neuro-oncological ventral antigen 2|www.ncbi.nlm.nih.gov/entrez/query.fcgi?db=gene&cmd=Retrieve&dopt=full_report&list_uids=384569 |
| 56. | NM_024246|MM8|transcript|chr3|88414579|88420360|ExemplarFor 'NM_024246'; gene_id '71913'; transcript_id 'NM_024246'; gene_name 'Tmem79'; alt '2310042N02Rik|2310074C17Rik'; transmembrane protein 79|www.ncbi.nlm.nih.gov/entrez/query.fcgi?db=gene&cmd=Retrieve&dopt=full_report&list_uids=71913 |
| 57. | NM_007457|MM8|transcript|chr5|137319620|137330687|ExemplarFor 'NM_007457'; gene_id '11769'; transcript_id 'NM_007457'; gene_name 'Ap1s1'; alt 'AP19'; adaptor protein complex AP-1, sigma 1|www.ncbi.nlm.nih.gov/entrez/query.fcgi?db=gene&cmd=Retrieve&dopt=full_report&list_uids=11769 |
| 58. | NM_010545|MM8|transcript|chr18|60929246|60938021|ExemplarFor 'NM_010545'; gene_id '16149'; transcript_id 'NM_010545'; gene_name 'Cd74'; alt 'CLIP|DHLAG|HLADG|Ia-GAMMA|Ii'; CD74 antigen (invariant polypeptide of major histocompatibility complex, class II antigen-associated)|www.ncbi.nlm.nih.gov/entrez/query.fcgi?db=gene&cmd=Retrieve&dopt=full_report&list_uids=16149 |
| 59. | NM_010819|MM8|transcript|chr6|123227735|123240884|ExemplarFor 'NM_010819'; gene_id '17474'; transcript_id 'NM_010819'; gene_name 'Clec4d'; alt 'Clecsf8|MGC117678|Mpcl|mMCL|mcl'; C-type lectin domain family 4, member d|www.ncbi.nlm.nih.gov/entrez/query.fcgi?db=gene&cmd=Retrieve&dopt=full_report&list_uids=17474 |

*Fig. 11 (Cont.)*

| Entry No. | Description |
|---|---|
| 60. | NM_011190|MM8|transcript|chr14|54541510|54545092|ExemplarFor 'NM_011190'; gene_id '19188'; transcript_id 'NM_011190'; gene_name 'Psme2'; alt 'AA589371|AI788882|PA28b'; proteasome (prosome, macropain) 28 subunit, beta|www.ncbi.nlm.nih.gov/entrez/query.fcgi?db=gene&cmd=Retrieve&dopt=full_report&list_uids=19188 |
| 61. | XM_988126|MM8|transcript|chr4|123592686|123592956|ExemplarFor 'XM_988126'; gene_id '667076'; transcript_id 'XM_988126'; gene_name 'LOC667076'; alt '-'; hypothetical protein LOC667076|www.ncbi.nlm.nih.gov/entrez/query.fcgi?db=gene&cmd=Retrieve&dopt=full_report&list_uids=667076 |
| 62. | NM_183256|MM8|transcript|chr15|99553680|99556148|ExemplarFor 'NM_183256'; gene_id '66379'; transcript_id 'NM_183256'; gene_name '2310016M24Rik'; alt 'AA959804|MGC106475'; RIKEN cDNA 2310016M24 gene|www.ncbi.nlm.nih.gov/entrez/query.fcgi?db=gene&cmd=Retrieve&dopt=full_report&list_uids=66379 |
| 63. | XM_988803|MM8|transcript|chr14|13599858|13600290|ExemplarFor 'XM_988803'; gene_id '667168'; transcript_id 'XM_988803'; gene_name 'LOC667168'; alt '-'; hypothetical protein LOC667168|www.ncbi.nlm.nih.gov/entrez/query.fcgi?db=gene&cmd=Retrieve&dopt=full_report&list_uids=667168 |
| 64. | XM_986077|MM8|transcript|chr17|27624207|27624561|ExemplarFor 'XM_986077'; gene_id '666801'; transcript_id 'XM_986077'; gene_name 'LOC666801'; alt '-'; similar to CG3950-PA|www.ncbi.nlm.nih.gov/entrez/query.fcgi?db=gene&cmd=Retrieve&dopt=full_report&list_uids=666801 |
| 65. | NM_025542|MM8|transcript|chr2|172131782|172161104|ExemplarFor 'NM_025542'; gene_id '66404'; transcript_id 'NM_025542'; gene_name '2410001C21Rik'; alt '1700067C04Rik|5730427M17Rik|AA589417'; RIKEN cDNA 2410001C21 gene|www.ncbi.nlm.nih.gov/entrez/query.fcgi?db=gene&cmd=Retrieve&dopt=full_report&list_uids=66404 |

*Fig. 11 (Cont.)*

EXOSOMAL BIOMARKERS DIAGNOSTIC OF TUBERCULOSIS

RELATED APPLICATIONS

This application claims priority under 35 U.S.C. § 119(e) to U.S. Provisional Patent Application No. 62/303,631 filed Mar. 4, 2016, which is incorporated herein by reference.

GOVERNMENT SUPPORT

This invention was made with government support under Grant No. RO1 AIO52439-06 awarded by the National Institutes of Health. The government has certain rights in the invention.

BACKGROUND OF THE INVENTION

*Mycobacterium tuberculosis* (Mtb) is an intracellular pathogen. Paradoxically, macrophages—whose purpose is to destroy such pathogens—provide both a primary niche for the bacterium's survival and replication, as well as acting as the major mediator of host protection through T cell-mediated activation of uninfected macrophages. Following infection, Mtb are phagocytosed by alveolar macrophages in the lung and subsequently colonize the underlying epithelial layer, which triggers recruitment of mononuclear cells from neighboring blood vessels that serve as host cells for multiplying bacteria and causing a condition of Tuberculosis (TB).

TB is a common and often lethal infectious disease caused by the *Mycobacterium* genus of bacteria, typically Mtb. According to the World Health Organization, one-third of the world population may be infected with Mtb and each year, is it estimated that over 8 million new cases, and almost 1.5 million deaths are caused by TB. This disease is particularly common in low to middle-income countries, accounting for roughly 80% of reported disease cases. Furthermore, the high prevalence of HIV in areas such as sub-Saharan Africa greatly adds to TB's lethality.

TB is air transmissible and, therefore, easily spreads between individuals through respiratory fluid droplets. Most Mtb infections are asymptomatic, latent TB infections (LTBI), however, some of these infections can eventually progress to active TB infections. TB typically infects the pulmonary system of an afflicted individual; however, the disease can also spread through the body causing extrapulmonary TB (EPTB). Roughly one in ten latent TB infections progresses to an active disease, which, if left untreated, typically kills more than 50% of those infected.

Given TB's high prevalence and associated deaths, fast diagnosis and treatment of active TB is of paramount importance. However, present diagnostic assays are often inaccurate, and are unable to distinguish between persons in the latent stage of the disease and those in the active stage. Moreover, available diagnostic tests are many times unable to distinguish between individuals who have been immunized, and individuals infected with TB.

Currently, the two most common methods of detecting Mtb infection are the sputum acid-fast bacilli smear microscopy test (AFB) and the tuberculin skin test (TST). In AFB smears, sputum is collected from patients and examined microscopically after a bacterial staining procedure. Although AFB can produce presumptive results in as little as a few hours, the test suffers from poor sensitivity. AFB also fails to identify TB patients having little to no Mtb in their sputum or those patients who are unable to produce sputum. This is especially common in young children or HIV infected patients. Further, Mtb replicates slowly, making positive identification of Mtb in cultures lengthy, ranging from days to weeks.

TST is a composite measure of cell-mediated immunity in response to TB antigen (PPD) stimulation, which is injected under the skin of a patient. However, it may take 2 to 3 days before the results can be obtained and frequently delivers false positive or false negative results. Also, this test does not distinguish latent infection from active disease, which is important in a diagnostic setting. Additionally, interferon-gamma based tests have also been developed. While these tests can provide rapid detection of Mtb, they too suffer from lack of sensitivity and specificity in certain situations. Moreover, both the cost of such tests, as well as the required expertise to perform such tests can be prohibitive.

Therefore, a need exists for a diagnostic and prognostic assay to identify those at risk for TB and capable of transmitting Mtb to other individuals. The detection of Mtb biomarkers in a patient's bodily fluid (blood, urine, etc.) provides such an opportunity. Therefore, the identification of specific and easily measured extracellular vesicle Mtb biomarkers may have a significant impact on global Mtb diagnosis and treatment. The present disclosure addresses these needs.

SUMMARY

The disclosure provides for methods of detecting extracellular vesicle RNA biomarkers to diagnose subjects with an active Mtb infection. The method generally comprises isolating—from bodily fluid of a subject—extracellular vesicles containing a plurality of RNA, extracting at least a portion of the RNA from the extracellular vesicles, and analyzing the RNA for the presence of one or more RNA, which, if detected, are indicative of an active Mtb infection, thereby determining the presence or absence of an active Mtb infection in the subject.

The disclosed methods provide several advantageous over the prior art. Most notably, embodiments of the disclosure do not rely on a subject's sputum sample as a source material to detect an active Mtb infection. Diagnostic tests using such samples suffer from poor sensitivity. Moreover, sputum samples may be difficult to collect from individuals suffering from secondary infections such as HIV. Instead, the disclosed methods allow the use of most any bodily fluid as a source for extracellular vesicle biomarkers. Sources such as blood, blood serum, blood plasma, and urine readily provide a vast pool of circulating biomarkers for diagnosis.

In certain embodiments of the disclosure, the biomarkers diagnostic of an active Mtb infection are certain RNA transcripts packaged and secreted in extracellular vesicles from Mtb infected cells. Such extracellular vesicles contain certain RNA from host cells, and RNA from Mtb. In some embodiments, the extracellular vesicle biomarkers may include at least one Mtb RNA selected from the group consisting of RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, and RV2024c. In other embodiments, the extracellular vesicle biomarker may include at least one host cell RNA selected from the group consisting of 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759 and 713.

In certain embodiments, the extracellular vesicles are exosomes.

Some embodiments of the method further include a means for detecting the RNA, which preferably, comprise a capture probe that may be a nucleotide sequence at least partially complementary to at least one of the RNA disclosed herein.

In other embodiments, the RNA biomarkers are amplified using RT-PCR for detection. In other certain embodiments, cDNAs are constructed from the RNA biomarkers.

The disclosure further provides for an RNA signature diagnostic of an active TB infection comprising certain RNA present in extracellular vesicles secreted from host cells infected with Mtb. The RNA signature may include at least one Mtb RNA selected from the group consisting of RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, and RV2024c. In other embodiments, the RNA signature may also may include at least one host cell RNA selected from the group consisting of 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759 and 713 wherein the host cell is a phagocytic white blood cell such as a macrophage, or any other host cell typically infected with Mtb.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 11 is a table showing host transcripts that were identified as being more abundant in exosomes released from infected macrophages relative to uninfected macrophages. Shown is the normalized log 2 transcript copy number for each of the 65 transcripts for each sequencing reaction which includes 3 replicates of exosomes from *M. tuberculosis* infected and 3 from uninfected macrophages. The information in the heading includes Microarray run number (X419442), date, cycle run number and whether it's from H37Rv-infected or uninfected (UN) macrophages. Diffm: Difference in expression levels (log 2) between the mean transcript expression levels in Rv exosomes to transcript levels in exosomes from uninfected macrophages. FC: fold change (conversion of the log 2 scale to decimal system).

DETAILED DESCRIPTION

Figure 1:
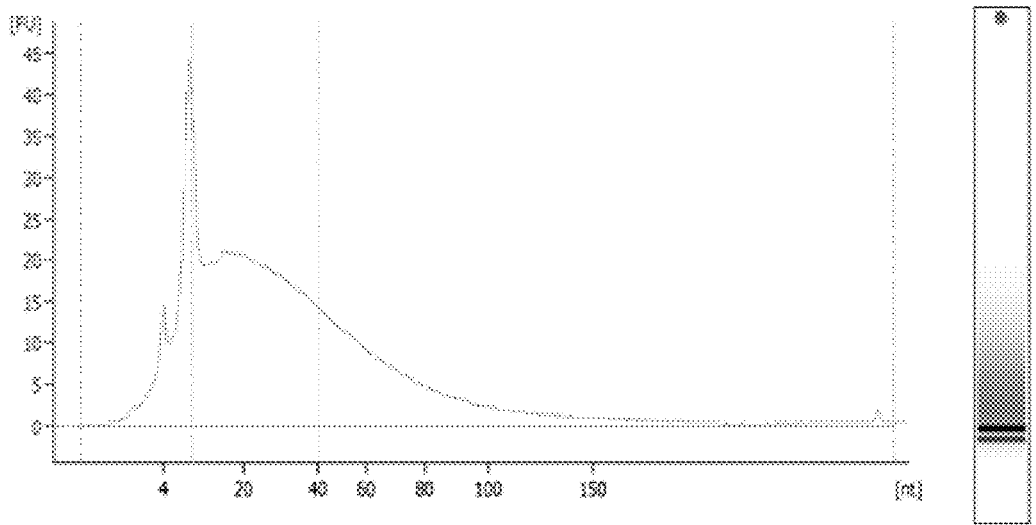
FIG. 1 illustrates exosomes derived from cell culture supernatants of Mtb-infected macrophages contain small RNA. Exosomes were isolated from cell culture supernatants of uninfected or Mtb-infected RAW264.7 macrophages. RNA was isolated from exosomes and tested on a Bioanalyzer small RNA pico chip (A). A Cartoon showing the steps involved in producing a cDNA library containing ligated Illumina adaptors used for RT-PCR (B). The cDNA libraries were analyzed on a Bioanalyzer for size distribution (C). 1, exosomes from uninfected cells; 2, exosomes from infected cells; 3, uninfected RAW 264.7 cells; 4, infected RAW 264.7 cells; 5, ligation control.
Figure 1:
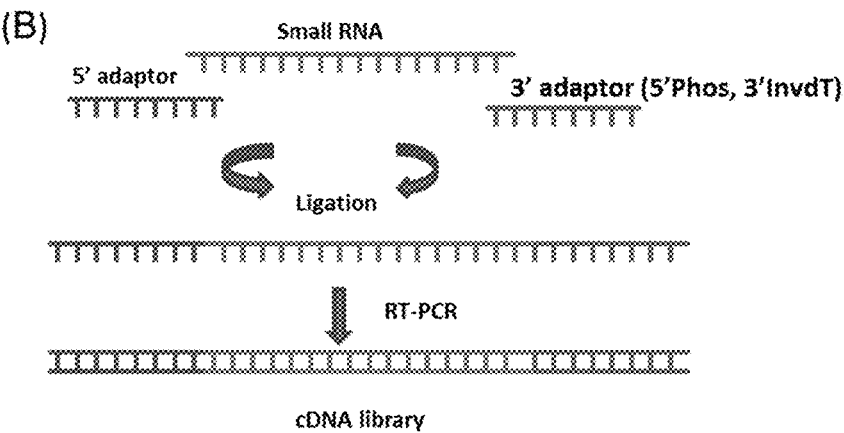
Figure 1:
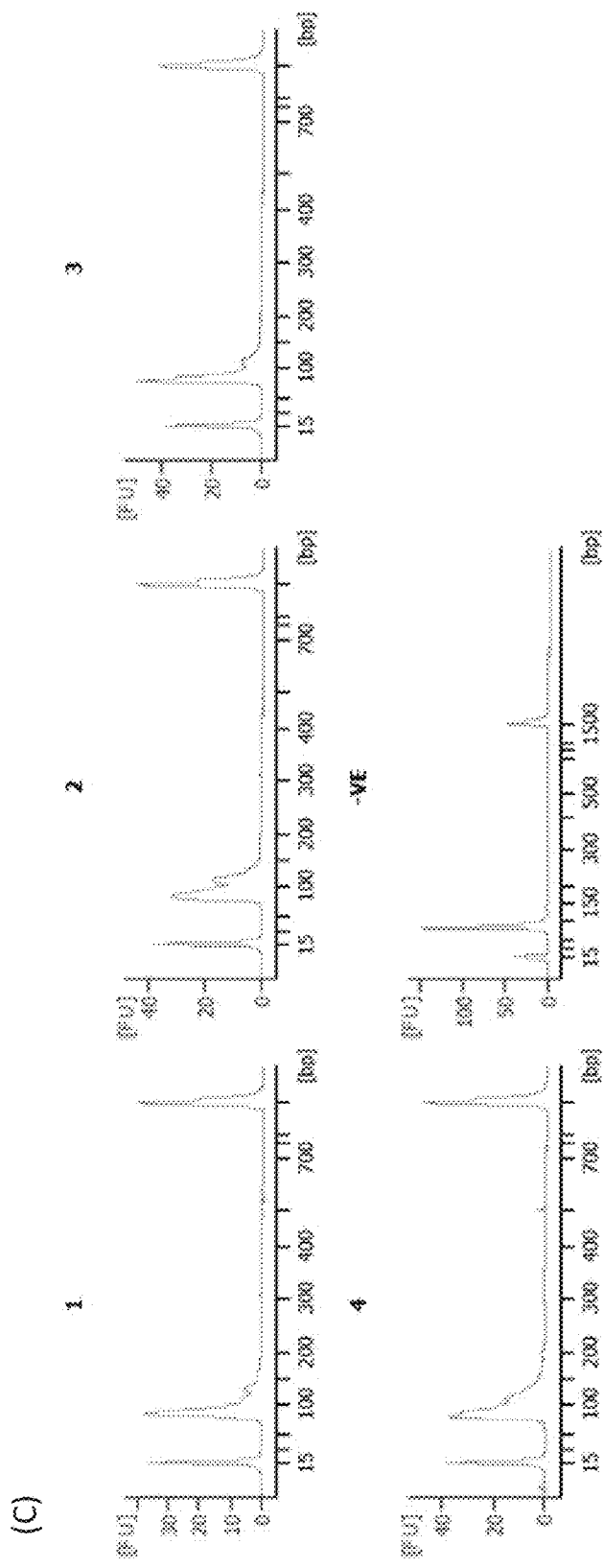

The present disclosure is based in part on the identification of an active *mycobacterium* infection signature including host miRNAs, mRNA transcripts as well as *mycobacterium* RNA present in extracellular vesicles derived from Mtb infected host cells. These Mtb RNAs are also present in extracellular vesicles isolated from the blood serum of TB infected individuals.

Accordingly, the disclosure is directed to a biomarker signature comprising certain Mtb and host RNAs found in secreted extracellular vesicles, as well as method of detecting the RNA signature to diagnose individuals with an active TB infection. As used herein, a "biomarker" is an anatomic, physiologic, biochemical, or molecular parameter associated with the presence of a specific physiological state or process, whether normal or abnormal, and, if abnormal, whether chronic or acute. Biomarkers are detectable and measurable by a variety of methods including laboratory assays and medical imaging. In some embodiments, a biomarker is a target protein.

In some embodiments, the biomarker is a plurality of RNA molecules extracted from an extracellular vesicle that, when present, is an RNA signature diagnostic of an active Mtb infection. One certain embodiment of an RNA signature diagnostic of an active *M. tuberculosis* infection may comprise at least one RNA isolated from an extracellular vesicle secreted from an *M. tuberculosis* infected cell. A further embodiment of the disclosure includes a method for identifying an active *M. tuberculosis* infection in a subject comprising the steps of isolating extracellular vesicles from bodily fluid of a subject, the extracellular vesicles contain a plurality of RNA, extracting at least a portion of the RNA from the extracellular vesicle, and analyzing the RNA for the presence of one or more RNA that are indicative of an active *M. tuberculosis* infection, thereby determining the presence or absence of an active *M. tuberculosis* infection in the subject.

The RNAs detected from isolated extracellular vesicles comprise one or more Mtb RNA sequences including RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, and RV2024c. The RNAs detected from isolated extracellular vesicles may also comprise one or more host RNA sequences including 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759 and 713. In various embodiments, the RNA is a host RNA listed in Table III below. Some embodiments may include a combination of both Mtb RNAs and host RNAs in the RNA signature.

The RNAs comprising the RNA signature diagnostic of an active TB infection may be analyzed using a detecting means. Preferably, the detection means includes a capture probe. A capture probe as used herein refers to a nucleic acid hybridization probe which is a fragment of DNA or RNA of variable length (usually 100-1000 bases long) which is used in DNA or RNA samples to selectively bind to and detect the presence of nucleotide sequences—the target nucleic acid, that is the RNA biomarkers disclosed herein—that are complementary to the sequence in the probe. The probe thereby hybridizes to single-stranded nucleic acid (DNA or RNA) whose base sequence allows probe-target base pairing due to complementarity between the probe and target. Probe-target hybridization is usually detected and quantified by fluorescence-based detection of fluorophore-labeled targets to determine relative abundance of nucleic acid sequences in the target.

The term "selective binding" as used herein refers to a measure of the capacity of a probe to hybridize to a target nucleotide sequence with specificity. Thus, the probe comprises a nucleotide sequence that is complementary, or essentially complementary, to at least a portion of the target nucleotide sequence.

The term "complementary" as used herein refers to those nucleic acid sequences which are base-pairing according to the standard Watson-Crick complementarity rules. As used herein, the term "complementary sequences" means nucleic acid sequences which are substantially complementary, as can be assessed by the same nucleotide comparison set forth below, or as defined as being capable of hybridizing to the nucleic acid segment in question under relatively stringent conditions such as those described herein.

A particular example of a contemplated complementary nucleic acid segment is an antisense oligonucleotide. With regard to probes disclosed herein having binding affinity to RNAs, the probe can be 100% complementary with the target polynucleotide sequence. However, the probe need not necessarily be completely complementary to the target nucleotide sequence along the entire length of the target nucleotide sequence so long as the probe can bind the target nucleotide sequence with specificity and capture it from the sample. For example, probes used may show 85%, 90%, 95%, 96%, 97% 98%, or 99% sequence identity with nucleotide sequences of any one or more of RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, RV2024c149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759, 713, and the transcripts listed in Table III below.

As will be understood to one of ordinary skill in the art, "percent identity," or "percent homology" when used herein to describe to a sequence, relative to a reference sequence, can be determined using the formula described by Karlin and Altschul (Proc. Natl. Acad. Sci. USA 87: 2264-2268, 1990, modified as in Proc. Natl. Acad. Sci. USA 90:5873-5877, 1993). Such a formula is incorporated into the basic local alignment search tool (BLAST) programs of Altschul et al. (J. Mol. Biol. 215: 403-410, 1990). BLAST nucleotide searches are performed with the NBLAST program, score+100, word length=12, to obtain nucleotide sequences homologous to a nucleic acid molecule of the invention. BLAST protein searches are performed with the XBLAST program, score=50, word length=3, to obtain amino acid sequences homologous to a reference polypeptide. To obtain gapped alignments for comparison purposes, Gapped BLAST is utilized as described in Altschul, et al. (Nucleic Acids Res. 25: 3389-3402, 1997). When utilizing BLAST and Gapped BLAST programs, the default parameters of the respective programs (e.g., XBLAST and NBLAST) are used. See http://www.ncbi.nlm.nik.gov.

"Stringent conditions" as used herein are those conditions that employ low ionic strength and high temperature for washing, for example, 0.015 M NaCl/0.0015 M sodium citrate/0.1% SDS at a temperature of at least 50° C., or employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer (pH 6.5) with 750 mM NaCl, 75 mM sodium citrate at 42° C. Another example is hybridization in 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at a temperature of at least 42° C., with washes at 42° C. in 0.2×SSC and 0.1% SDS. A skilled artisan can readily determine and vary the stringency conditions appropriately to obtain a clear and detectable hybridization signal.

In some embodiments, it may be advantageous to measure the level of the RNA biomarker. In some embodiments, RNA levels may be measured by reverse transcription quantitative polymerase chain reaction (RT-PCR followed with qPCR). RT-PCR is used to create a cDNA from the mRNA. The cDNA may be used in a qPCR assay to produce fluorescence as the DNA amplification process progresses. By comparison to a standard curve, qPCR can produce an absolute measurement such as number of copies of RNA present in a sample (Wang et al., PloS ONE 2011; 6: e25832; Gallo et al., PloS ONE 2012; 7: e30679.; Sinha et al., The Journal of Allergy and Clin Immunol. 2013; 132: 219-222.). Nucleic acid molecules of the present disclosure (i.e., synthetic oligonucleotides) may be used as probes or specific primers for PCR. Such molecules can easily be synthesized by chemical techniques, for example, the phosphotriester method of Matteucci et al. (1981) J. Am. Chem. Soc. 103, 3185-3191 or using automated synthesis methods. Furthermore, Northern blots, microarrays, Invader assays, and RT-PCR combined with capillary electrophoresis have all been used to measure expression levels of RNA in a sample. (See Gene Expression Profiling: Methods and Protocols, Richard A. Shimkets, editor, Humana Press, 2004.)

In some embodiments, a nucleic acid sequence may incorporate modified nucleotides, such as methylated, biotinylated, or fluorinated nucleotides; and nucleotide analogs, such as dye-labeled or fluorescent nucleotides (e.g. 3-methylisoxanthopterin, 6-methylisoxanthopterin, 4-amino-6-methyl-8-(2-deoxy-beta-d-ribofuranosyl)-7(8H)-pteridone (6-MAP), 2-amino purine, pyrrolo-c, or 1,3-Diaza-2-oxo-phenothiazine), non-hydrolysable nucleotides, or nucleotides comprising heavy atoms (Hawkins et al., U.S. Pat. No. 6,716,971). Such reagents are widely available from a variety of vendors, including Perkin Elmer and Sigma-Aldrich.

In some embodiments, the RNA level(s) data is generated from a microarray, such as a gene chip. A microarray as employed herein includes RNA or DNA arrays. A gene chip is essentially a microarray—that is to say an array of discrete regions, typically nucleic acids—which are separate from one another and are, for example arrayed at a density of between, about $100/cm^2$ to $1000/cm^2$, but can be arrayed at greater densities such as $10000/cm^2$.

A microarray consists of an arrayed series of a plurality of microscopic spots of nucleotides, called features, each containing a small amount (typically in the range of picomoles) of a specific nucleotide sequence. The specific nucleotide sequence can be a short section of a gene or other nucleotide element that is used as a probe to hybridize a cDNA or cRNA sample under high-stringency conditions. Probe-target hybridization is usually detected and quantified by fluorescence-based detection of fluorophore-labeled targets to determine relative abundance of nucleic acid sequences in the target. The nucleotide probes are typically attached to a solid surface by a covalent bond to a chemical matrix (via epoxy-silane, amino-silane, lysine, polyacrylamide or others). Examples of microarrays used to determine measure nucleic acid levels include U.S. Pat. No. 6,271,002, et al; U.S. Pat. Nos. 6,218,122; 6,218,114; or 6,004,755.

"Solid support" as used herein to any substrate having a surface to which molecules may be attached, directly or indirectly, through either covalent or non-covalent bonds. A "solid support" can have a variety of physical formats, which can include, for example, a membrane; a chip (e.g., a protein chip); a slide (e.g., a glass slide or coverslip); a column; a hollow, solid, semi-solid, pore- or cavity-containing particle, such as, for example, a bead; a gel; a fiber, including a fiber optic material; a matrix; and a sample receptacle. Exemplary sample receptacles include sample wells, tubes, capillaries, vials, and any other vessel, groove or indentation capable of holding a sample. A sample receptacle can be contained on a multi-sample platform, such as a microtiter plate, slide, microfluidics device, and the like. A support can be composed of a natural or synthetic material, an organic or inorganic material. The composition of the solid support on which capture reagents are attached generally depends on the method of attachment (e.g., covalent attachment). Other exemplary receptacles include microdroplets and microfluidic controlled or bulk oil/aqueous emulsions within which assays and related manipulations can occur. Suitable solid supports include, for example, plastics, resins, polysaccharides, silica or silica-based materials, functionalized glass, modified silicon, carbon, metals, inorganic glasses, membranes, nylon, natural fibers (such as, for example, silk, wool and cotton), polymers, and the like. The material composing the solid support can include reactive groups such as, for example, carboxy, amino, or hydroxyl groups, which are used for attachment of the capture reagents. Polymeric solid supports can include, e.g., polystyrene, polyethylene glycol tetraphthalate, polyvinyl acetate, polyvinyl chloride, polyvinyl pyrrolidone, polyacrylonitrile, polymethyl methacrylate, polytetrafluoroethylene, butyl rubber, styrenebutadiene rubber, natural rubber, polyethylene, polypropylene, (poly)tetrafluoroethylene, (poly)vinylidenefluoride, polycarbonate, and polymethylpentene. Suitable solid support particles that can be used include, e.g., encoded particles, such as Luminex®-type encoded particles, magnetic particles, and glass particles.

For some nucleotide arrays, short 20-25mers nucleotide sequences may be synthesized in situ, either by photolithography onto silicon wafers (high-density-oligonucleotide arrays from Affymetrix) or by ink-jet technology (developed by Rosetta Inpharmatics and licensed to Agilent Technologies).

Alternatively, pre-synthesized nucleotide sequences may be printed onto glass slides. Methods based on synthetic nucleotide sequences offer the advantage that because sequence information alone is sufficient to generate the DNA to be arrayed, no time-consuming handling of cDNA resources is required. Also, probes can be designed to represent the most unique part of a given target sequence, making the detection of closely related nucleic acid sequences possible.

In some embodiments, a microarray may contain cDNA at least partially complementary to one or more RNA sequences including RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, RV2024c, 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759 and 713, and/or a transcript listed in Table III below.

A biomarker microarray may be processed in manual, semi-automatic or automatic modes. Manual mode refers to manual operations for all assay steps including reagent and sample delivery onto microarrays, sample incubation and microarray washing. Semi-automatic modes refer to manual operation for sample and reagent delivery onto microarray, while incubation and washing steps operate automatically. In an automatic mode, three steps (sample/reagent delivery, incubation and washing) can be controlled by a computer or an integrated breadboard unit with a keypad. For example, the microarray can be processed with a ProteinArray Workstation (PerkinElmer Life Sciences, Boston, Mass.) or Assay 1200™. Workstation (Zyomyx, Hayward, Calif.). Scanners by fluorescence, colorimetric and chemiluminescence, can be used to detect microarray signals and capture microarray images. Quantitation of microarray-based assays can also be achieved by other means, such as mass spectrometry and surface plasma resonance. Captured microarray images may be analyzed by stand-alone image analysis software or with image acquisition and analysis software package. For example, quantification of an antigen microarray can be achieved with a fluorescent PMT-based scanner—ScanArray 3000 (General Scanning, Watertown, Mass.) or colorimetric CCD-based scanner—VisionSpot (Allied Biotech, Ijamsville, Md.). Typically, the image analysis would include data acquisition and preparation of assay report with separate software packages. In order to expedite the whole assay process from capturing an image to generating an assay report, all the analytical steps including image capture, image analysis, and report generation, can be confined in and/or controlled by one software package. Such a unified control system would provide the image analysis and the generation of assay report in a user-friendly manner.

In some embodiments, a method may include comparison to a reference or control sample. The reference can include, for example, a level of the one or more RNAs (e.g., Mtb RNA or Host cell RNA) in one or more samples from one or more individuals without TB. In some embodiments, the reference includes a level of the one or more RNAs in a sample from the subject taken over a time course. In some embodiments, the reference includes a sample from the subject collected prior to initiation of treatment for TB and/or onset of the TB and the biological sample is collected after initiation of the treatment or onset of the TB.

In other embodiments, a measured increase or decrease in the presence of certain RNA biomarkers isolated from secreted extracellular vesicles may indicate, or aid in the detection of an active TB infection. For example, a 2-fold increase in host cell RNA (compared to a control sample, e.g. an uninfected subject) as determined using qRT-PCR or similar means may be indicative of an active TB infection. Exemplary RNAs which, if shown to have a 2-fold increase, may be indicative of an active TB infection are shown in Table I below.

In other embodiments, the exosomal RNAs are extracted from the exosomes using a buffer comprised of 4 M GuSCN, 0.1 M beta-mercaptoethanol, 0.5% N-lauroyl sarcosine, 25 mM Na-citrate, pH 7.2. The final RNA material is stored in 0.1 mM EDTA. Exemplary RNAs which, if shown to have a 2-fold increase, may be indicative of an active TB infection are shown in Table III below.

Extracellular Vesicles

Extracellular vesicles are small lipid membrane enclosed vesicles that are released into the extracellular environment from a variety of different cells such as but not limited to, cells that originate from, or are derived from, the ectoderm, endoderm, or mesoderm including any such cells that have undergone genetic, environmental, and/or any other variations or alterations (e.g. bacterial/virally infected cells, tumor cells or cells with genetic mutations). In certain preferred embodiments, the extracellular vesicles are secreted from macrophage cells or the like. More preferably, the macrophage cells are infected with Mtb.

Extracellular vesicles may include, for example, circulating microvesicles (cMVs), microvesicle, exosome, nanovesicle, dexosome, bleb, blebby, prostasome, microp article, intralumenal vesicle, membrane fragment, intralumenal endosomal vesicle, endosomal-like vesicle, exocytosis vehicle, endosome vesicle, endosomal vesicle, apoptotic body, multivesicular body, secretory vesicle, phospholipid vesicle, liposomal vesicle, argosome, texasome, secresome, tolerosome, melanosome, oncosome, or exocytosed vehicle.

In preferred embodiments, the RNA biomarkers are encapsulated in excreted exosomes. An exosome is typically created intracellularly when a segment of the cell membrane spontaneously invaginates and is ultimately exocytosed. As used herein, exosomes can also include any shed membrane bound particle that is derived from either the plasma membrane or an internal membrane. Exosomes can also include cell-derived structures bounded by a lipid bilayer membrane arising from both herniated evagination (blebbing) separation and sealing of portions of the plasma membrane or from the export of any intracellular membrane-bounded vesicular structure containing various membrane-associated proteins, including surface-bound molecules derived from the host circulation that bind selectively to the exosomal proteins together with molecules contained in the exosome lumen, including but not limited to mRNAs, microRNAs or intracellular proteins. Blebs and blebbing are further described in Charras et al, *Nature Reviews Molecular and Cell Biology*, Vol. 9, No. 11, p. 730-736 (2008). Exosomes can also include membrane fragments.

Extracellular vesicles, and in particular, exosomes, may have, but not be limited to, a diameter of greater than about 10, 20, or 30 nm. They can have a diameter of about 30-1000 nm, about 30-800 nm, about 30-200 nm, about 30-100 nm, about 20 nm to about 100 nm, about 30 nm to about 150 nm, about 30 nm to about 120 nm, about 50 nm to about 150 nm, or about 50 nm to about 120 nm. In some embodiments, the exosomes can have, but not be limited to, a diameter of at least 20 nm and less than about 1000 nm, 800 nm, 500 nm, 200 nm, 100 nm, or 50 nm. As used throughout, the term "about," when referring to a value or to an amount is meant to encompass variations in some embodiments±10% from the specified amount, as such variations are appropriate.

Isolation of Extracellular Vesicles

Exosomes and other extracellular vesicles may be directly assayed from the biological samples, such that the level of exosomes is determined or the one or more biomarkers of the exosomes are determined without prior isolation, purification, or concentration of the exosomes.

Alternatively, in some embodiments, an exosome may be purified or concentrated prior to analysis. Analysis of an exosome can include quantitating the amount of one or more exosome populations of a biological sample. For example, a heterogeneous population of exosomes can be quantitated, or a homogeneous population of exosomes, such as a population of exosomes with a particular biomarker profile, or derived from a particular cell type (cell-of-origin specific exosomes) can be isolated from a heterogeneous population of exosomes and quantitated. Analysis of an exosome can also include detecting, quantitatively or qualitatively, a particular biomarker profile or a bio-signature, of an exosome. An enriched population of exosomes can be obtained from a biological sample derived from any cell or cells capable of producing and releasing exosomes into the bodily fluid.

In a preferred embodiment, the biological sample of an individual with active TB is taken from the blood, blood serum, blood plasma or urine. One skilled in the art will recognize that a biological sample can also be taken from, but not limited to the following bodily fluids: peripheral blood, ascites, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation that may be of fetal or maternal origin. The biological sample may also be a tissue sample or biopsy, from which exosomes may be obtained.

As used herein, "individual" and "subject" are used interchangeably to refer to a test subject or patient. The individual can be a mammal or a non-mammal. In various embodiments, the individual is a mammal. A mammalian individual can be a human or non-human. In various embodiments, the individual is a human. A healthy or normal individual is an individual in which the disease or condition of interest (such as TB) is not detectable by conventional diagnostic methods.

Exosomes and other extracellular vesicles may be concentrated or isolated from a biological sample using size exclusion chromatography, density gradient centrifugation, differential centrifugation, nanomembrane ultrafiltration, immunoabsorbent capture, affinity purification, microfluidic separation, commercially available protein purification kits, or combinations thereof.

In some embodiments, size exclusion chromatography, such as gel permeation columns, centrifugation or density gradient centrifugation, and filtration methods can be used. For example, exosomes can be isolated by differential centrifugation, anion exchange and/or gel permeation chromatography, sucrose density gradients, organelle electrophoresis, magnetic activated cell sorting (MACS), or with a nanomembrane ultrafiltration concentrator. Various combinations of isolation or concentration methods can be used.

Highly abundant proteins, such as albumin and immunoglobulins, may hinder isolation of exosomes from a biological sample. Therefore, exosomes may be isolated from a biological sample using a system that utilizes multiple antibodies that are specific to the most abundant proteins found in blood. Such a system can remove up to several proteins at once, thus unveiling the lower abundance species such as cell-of-origin specific exosomes.

This type of system can be used for isolation of exosomes from biological samples such as blood, blood serum, blood plasma, cerebrospinal fluid, urine and/or saliva. The isolation of exosomes from a biological sample may also be enhanced by high abundant protein removal methods as described in Chromy et al. J. Proteome Res 2004; 3: 1120-1127. In another embodiment, the isolation of exosomes from a biological sample may also be enhanced by removing serum proteins using glycopeptide capture as described in Zhang et al, Mol Cell Proteomics 2005; 4: 144-155. In addition, exosomes from a biological sample such as urine may be isolated by differential centrifugation followed by contact with antibodies directed to cytoplasmic or anti-cytoplasmic epitopes as described in Pisitkun et al., *Proc Natl Acad Sci USA,* 2004; 101: 13368-13373.

In some embodiments, the exosomal RNAs are extracted from the exosomes using a buffer comprised of 4 M GuSCN, 0.1 M beta-mercaptoethanol, 0.5% N-lauroyl sarcosine, 25 mM Na-citrate, pH 7.2. The final RNA material can be stored in 0.1 mM EDTA or a similar buffer system, as would be recognized by one of skill in the art.

Kits

The present disclosure is also directed to a kit or system useful for practicing the methods described herein. The kit can be a packaged combination of one or more containers, devices, or the like holding the necessary reagents, and usually including written instructions for the performance of assays. The kit may include containers to hold the materials during storage, use or both. Furthermore, any kit can contain one or more detectable labels as described herein, such as a fluorescent moiety, etc. In some embodiments, a kit includes (a) one or more capture probe (such as, for example, at least one nucleic acid) for detecting one or more RNA biomarkers in a biological sample, and optionally (b) one or more software or computer program products for predicting whether the individual from whom the biological sample was obtained suffers from or is infected with TB. Alternatively, rather than one or more computer program products, one or more instructions for manually performing the above steps by a human can be provided.

In some embodiments, a kit comprises a solid support, a capture probe, and a signal generating material. The kit can also include instructions for using the devices and reagents, handling the sample, and analyzing the data. Further the kit may be used with a computer system or software to analyze and report the result of the analysis of the biological sample. The kits can also contain one or more reagents (e.g., solubilization buffers, detergents, washes, or buffers) for processing a biological sample. Any of the kits described herein can also include, e.g., buffers, blocking agents, positive control samples, negative control samples, software and information such as protocols, guidance and reference data.

In some embodiments, kits are provided for the analysis of an active Mtb infection, wherein the kits comprise PCR primers for one or more RNA biomarkers described herein. In some embodiments, a kit may further include instructions for use and correlation of the biomarkers with TB diagnosis. In some embodiments, a kit may include a DNA array containing the complement (cDNA) of one or more of the biomarkers including RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, RV2024c, 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759, 713, and/or a transcript from Table III, reagents, and/or enzymes for amplifying or isolating sample DNA. The kits may include reagents for RT-PCR, real-time PCR, probes and/or primers, and enzymes. A kit may comprise reagents comprising at least one capture probe for determining the level of one or more biomarkers in a test sample.

Definitions

Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: A Comprehensive Desk Reference, published by Wiley, John & Sons, Inc., 1995 (ISBN 0471186341).

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The following examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Exosomal RNA Released from *Mycobacterium tuberculosis* Infected Cells Exosomes released from macrophages infected with *M. tuberculosis* (Mtb) or treated with mycobacterial culture filtrate proteins as well as exosomes isolated from Mtb-infected mice have been characterized for their protein cargo and have been shown to promote both innate and acquired immune responses in vitro and in vivo. However, it is not known whether the RNA present in these exosomes contributes to this immune response. To address this question requires characterization of the RNA content within the exosomes. In the present study, exosomes released from Mtb-infected macrophages showed the exosomes to contain host miRNAs and messenger RNAs. While a general diminished level of host miRNAs in exosomes from infected cells was observed, also observed was a subset of miRNAs and mRNA transcripts unique to these exosomes. These results suggest that there is selective packaging of RNA content in exosomes following an Mtb infection. The exosomal RNA could be transferred to and translated in recipient cells and could elicit a biologically response in these cells. Surprisingly, mycobacterial transcripts were also detected in in exosomes released from Mtb-infected macrophages and from extracellular vesicles derived from TB patient serum. Accordingly, this is the first study to show the presence of pathogen-derived RNA in exosomes released during a bacterial infection.

Results

Defining the miRNA Content within Exosomes Derived from M. tuberculosis-infected and Uninfected RAW264.7 Cells Exosomes were isolated from the culture supernatants of uninfected and Mtb-infected RAW264.7 macrophages. We obtained approximately 25 µg of exosomes from $1 \times 10^7$ cells. Exosomes were analyzed and were of the expected size and composition (data not shown). Total RNA was isolated from 400 µg of exosomes and analyzed for quality and size distribution on an Agilent bioanalyzer. As shown in FIG. 1A, we observed predominantly small RNA in the exosomes and no detectable tRNA. To eliminate any potential contaminating RNA attached to exosomes, the exosomes were treated with RNAse A prior to RNA isolation. To further characterize the small RNA content in exosomes, cDNA libraries were constructed using the small RNA population derived from exosomes or from donor macrophages (FIGS. 1B and 1 C). Since we wished to maximize coverage of miRNA sequences within exosomes, we biased our cDNA loading onto the 454 Sequencer to include 25% volume for each exosome library, 20% for each donor cell library and 10% for negative control. Therefore, we did not interpret quantitative differences between miRNAs from the sequencing data. After trimming of adaptor and primer sequences from our reads, a megablast was performed against the mature mouse miRNAs in mirbase. Using 1 as the cutoff E value we identified 52 and 57 miRNAs in exosomes released from uninfected and infected cells respectively. We also identified 57 and 80 miRNAs present in uninfected and infected RAW264.7 cells respectively (Table I).

Approximately 60% of the miRNAs were present in exosomes from both infected and uninfected macrophages including the miRNAs Mmu 99b-5p, Mmu 30c, Mmu 30a, Mmu 191, Mmu 378, Mmu 210, Mmu 423-5p & Mmu 486-5p which have been previously reported to be expressed following mycobacterial infection both in vitro and in vivo. From the cohort of miRNAs identified in exosomes, a subset was further selected for validation by PCR or by SYBR Green based quantitative PCR.

Figure 2:
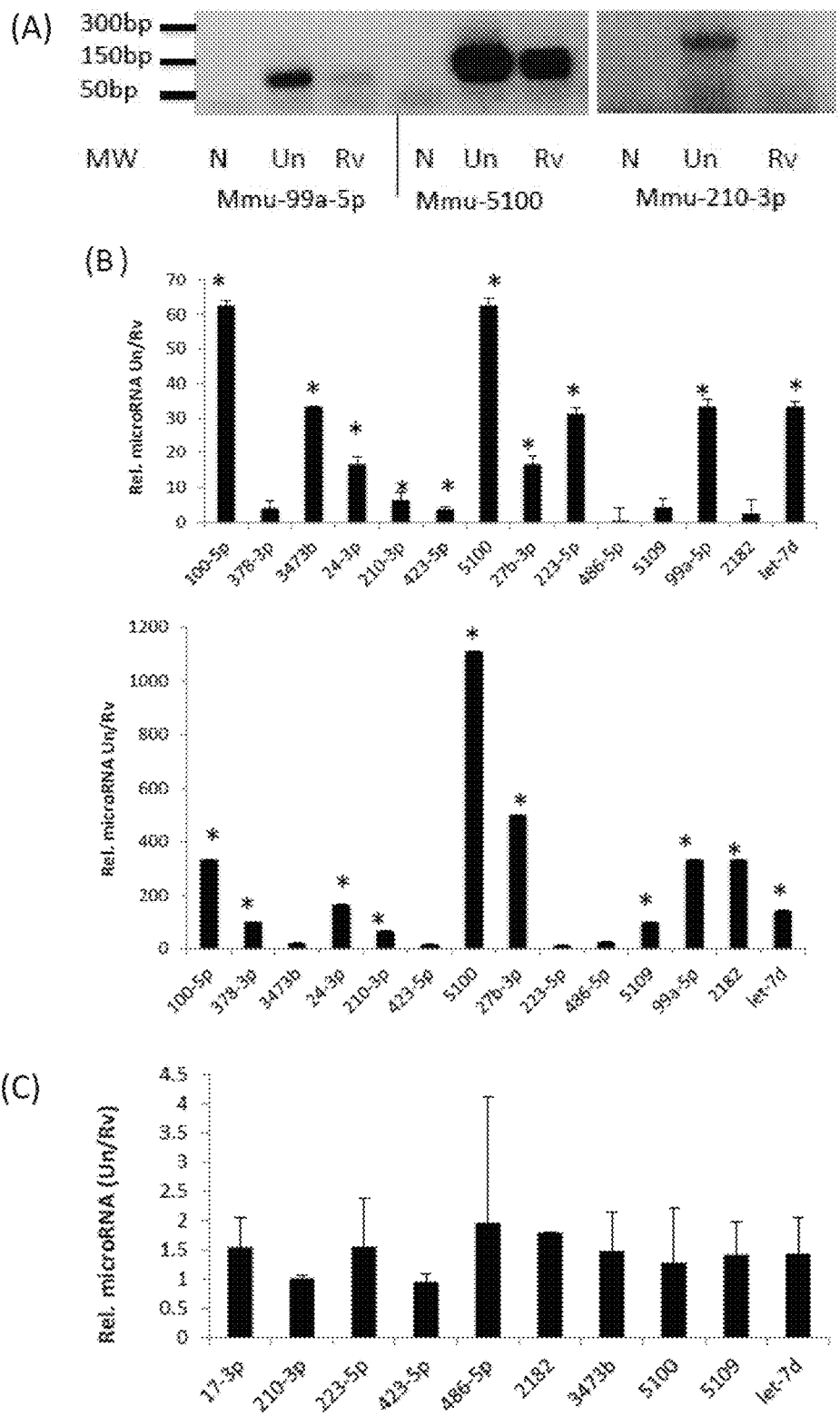
FIG. 2 illustrates exosomes released from Mtb-infected macrophages show limited incorporation of host miRNAs. Total RNA was isolated from exosomes and reverse transcribed using miR-Script cDNA synthesis kit. PCR was performed for selected miRNAs using miRNA specific forward primers and a universal reverse primer (A). Quantitative PCR was performed on selected miRNAs using sno234 as the endogenous miRNA control (B). Selected miRNAs that showed limited incorporation into exosomes released from infected RAW264.7 cells were analyzed for expression levels from both infected and uninfected cells (C). N; no template control, Un; exosomes from uninfected cells, Rv; exosomes from infected cells. Results were drawn from three independent experiments with standard deviations.

For these experiments, RNA was isolated from independent preparations of exosomes and results were drawn from three experimental replicates. Total RNA was polyadenylated and converted to cDNA and PCR amplified using miRNA specific primer and PerfeCTa universal primer (FIG. 2A). For qPCR validation, we tested different endogenous controls for miRNAs including U6, Sno202, Sno135 and Sno234 which have been used previously. Of these different controls, only Sno234 showed similar $C_t$ values across all exosome cDNAs and therefore was used as an endogenous control for all subsequent experiments.

Quantitative PCR on selected miRNAs showed an overall suppression of these miRNAs ranging from 5 to 100-fold in exosomes from infected compared to uninfected cells (FIG. 2B). However, we failed to observe any down-regulation of this subset of miRNAs in RAW264.7 cells following a mycobacterial infection (FIG. 2c). To determine if the down-regulation of miRNAs was related to pathogenicity, we quantified expression of select miRNAs in exosomes released from RAW264.7 cells infected with non-pathogenic M. smegmatis. We observed a similar down-regulation of miRNAs relative to uninfected exosomes (Unpublished observation). Our results suggest that mycobacterial infection of macrophages results in the general inhibition of miRNA incorporation into exosomes. To understand the significance behind this suppression we evaluated the quan-

TABLE I

Mouse miRNAs identified in exosomes and RAW 264.7 macrophages by 454 sequencing of the small RNA libraries (BLASTn against mature mirBase, E = 1).

| Un Exo | Rv Exo | Un RAW | Rv RAW |
|---|---|---|---|
| 1224-3p, 16-5p,* 195-5p,* 182-5p, 17-3p,* 100-5p, 1895,* 193-3p,* 101a-3p, 101c, 101b-3p, 101a-5p, 183-5p, 1898,* 140-3p, 139-3p,* 140-5p, 191-5p, 152-5p, 210-3p, 223-5p,* 27b-3p, 27a-3p, 21-3p,* 20b-3p,* 2182, 3473b, 3473, 3473d, 30a-3p,* 30e-3p,* 30d-3p,* 351-5p,* 341-3p, 30c-2-3p, 30c-1-3p, 370-3p,* 3089-3p,* 378-3p, 378b, 378-5p, 345-5p, 423-5p, 5100, 5128, 5109,* 709, 99b-5p, 99a-5p, let 7d-3p,* let 7d-5p,* let7a-5p* | 152-5p, 101b-3p, 101a-3p, 101c, 101a-5p, 149-3p,* 100-5p, 181c-5p,* 1839-3p,* 1224-3p, 191-5p, 140-3p, 140-5p, 151-3p,* 182-5p, 183-5p, 210-3p, 27b-3p, 27a-3p, 24-3p, 214-3p,* 2182, 292-3p,* 378-3p, 378b, 378-5p, 345-5p, 3473b, 3473, 3473d, 3107-5p,* 3074-5p,* 341-3p, 344i,* 30c-2-3p, 30c-1-3p, 423-5p, 486-5p,* 486-3p,* 434-5p,* 598-3p,* 5099,* 5113,* 5100, 5106,* 5128, 5097,* 5621-5p,* 5115,* 5111-5p,* 709, 714,* 99a-5p, 99b-5p, 877-3p,* 759, 713* | 151-3p, 191-5p, 140-3p, 146b-5p, 146a-5p, 146a-3p, 1196-5p, 152-5p, 10a-5p,* 10b-5p,* 182-5p, 193a-3p, 193b-3p, 183-5p, 1195, 1935, 140-5p, 192-5p,* 1898,* 210-3p, 27b-3p, 27a-3p, 29a-3p, 24-3p, 29c-3p, 25-3p,* 29b-3p, 215-3p,* 2182, 378b, 378-3p, 378-5p, 345-5p, 3074-5p, 30a-3p, 30e-3p, 30d-3p, 339-3p,* 3473b, 3473, 3473d,* 471-5p, 423-5p,* 5100, 5097, 532-5p, 582-5p,* 5109, 5621-5p, 5128, 709, 700-3p,* 92a-3p,* 93-5p, let7d-5p,* let7a-5p, let7c-5p | 146b-5p, 146a-5p, 146a-3p, 182-5p, 101b-3p,* 101a-3p,* 101c,* 101a-5p,* 1306-5p,* 183-5p, 151-3p, 100-5p,* 152-5p, 140-3p, 191-5p, 1198-5p,* 140-5p, 193a-3p, 193b-3p, 17-5p,* 106a-5p,* 181c-5p,* 16-5p,* 195-5p,* 107-3p,* 103-3p,* 1935, 1196-5p, 1195, 1198-3p,* 210-3p, 2182, 2137,* 27a-3p, 27b-3p, 21-5p,* 24-3p, 21-3p,* 211-3p,* 20b-5p,* 20a-5p,* 207,* 29a-3p, 29c-3p, 29b-3p, 30e-3p, 30a-3p, 3473b, 3473, 378-3p, 378b, 345-5p, 3967,* 3965,* 30d-3p, 3074-5p, 3960,* 378-5p, 320-3p,* 3067-3p,* 471-5p, 494-3p,* 5100, 5099,* 5128, 532-5p, 5097, 5106,* 5109, 5115,* 5621-5p, 5111-5p,* 709, 720,* 99b-5p,* 99a-5p,* 93-5p, let7c-5p, let7b-5p,* let7a-5p |

*Unique to each group tified miRNAs for mRNA targets using the miRDB and functional KEGG pathway analysis. The analysis showed that the gene targets for these miRNAs included those associated with immune surveillance and inflammation (Table II).

TABLE II

Functional pathways identified in mRNA targets for the selected miRNA.

| Pathway | Number of genes | Gamma corrected p value |
| --- | --- | --- |
| Calcium signaling pathway | 8 | 0.00157555 |
| Neuroactive ligand-receptor interaction | 9 | 0.00213164 |
| Pathways in cancer | 9 | 0.0105228 |
| MAPK signaling pathway | 7 | 0.02555087 |
| ErbB signaling pathway | 9 | 5.05E−05 |
| Natural killer cell mediated cytotoxicity | 8 | 5.05E−05 |
| GnRH signaling pathway | 7 | 0.00287188 |
| Jak-STAT signaling pathway | 8 | 0.01062047 |
| Ubiquitin mediated proteolysis | 7 | 0.02275327 |
| Melanogenesis | 6 | 8.39E−04 |

Figure 3:
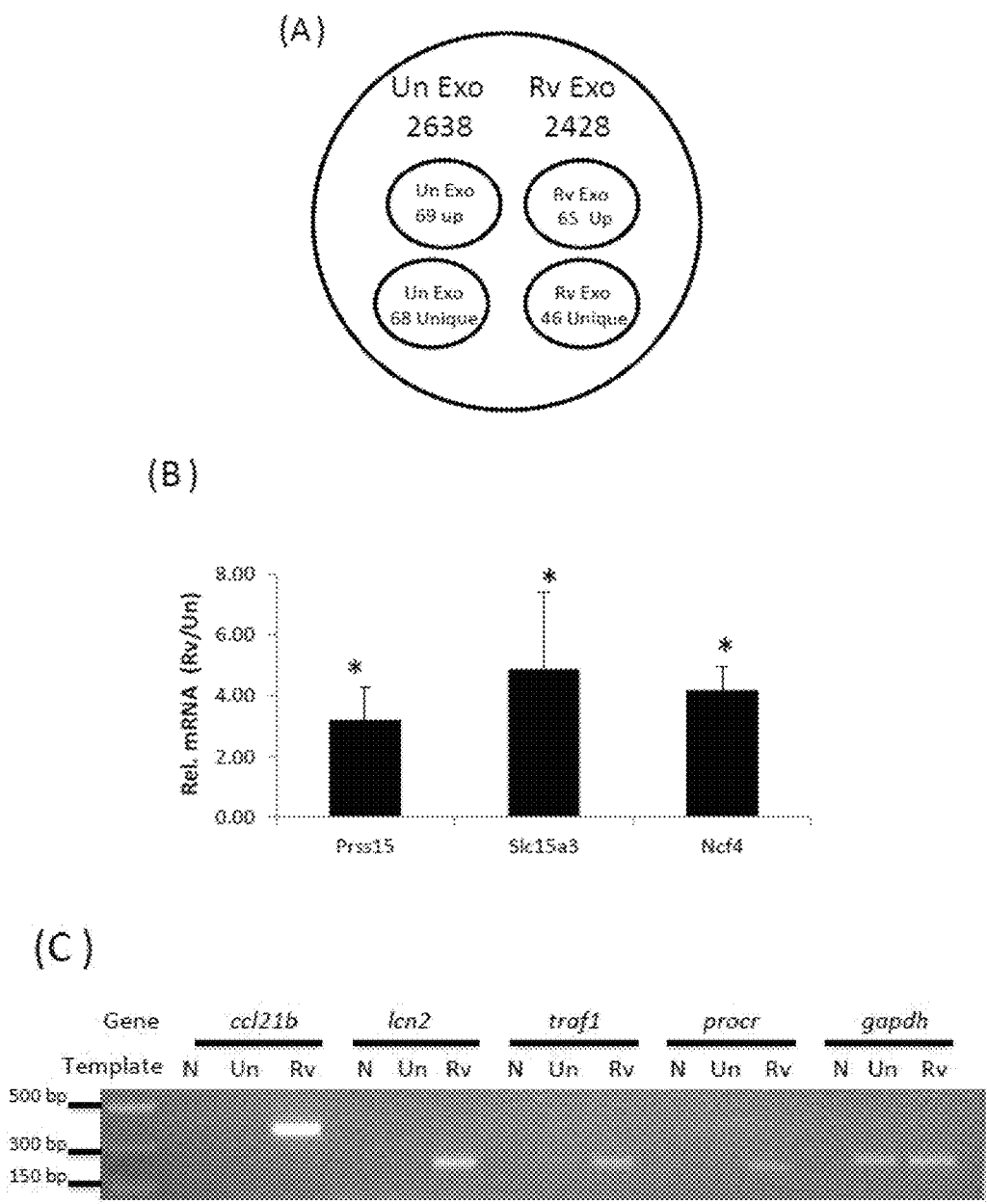
FIG. 3 illustrates a unique set of host transcripts detected in exosomes isolated from Mtb-infected macrophages. Total RNA was isolated from exosomes and cells, reverse transcribed, labeled with Cy3 and hybridized onto whole mouse genome arrays. The signal intensities were converted to expression values and transcripts were identified that had expression values above empty well values for all three experimental replicates (A). Three representative transcripts from the cohort of genes defined by array analysis as highly expressed in exosomes from infected RAW264.7 cells were validated for quantitative differences compared to uninfected exosomes by SYBR Green based qRT-PCR (B). Five transcripts that were unique to exosomes from infected cells were further validated by PCR. Primers were designed for specific transcripts and exosomal RNA was derived from independent exosome preparations (C). Exo; exosomes, N; no template control, Un; exosomes from uninfected cells, Rv; exosomes from infected cells. Results are representative of three independent experiments for both the microarray analysis and qRT-PCR validation which includes standard deviations.

Profiling the mRNA Transcripts within Exosomes Released from Infected and Uninfected RAW 264.7 Cells A microarray analysis was undertaken to identify the host mRNA signatures present in exosomes. In order to generate the 1 μg of total RNA needed for the gene expression studies we used approximately 400 μg of exosomes. To determine enrichment of specific transcripts in exosomes following mycobacterial infection, exosomal RNA from uninfected cells and cellular RNA from uninfected or Mtb-infected donor macrophages were used for comparison. We identified 2428 and 2638 transcripts in exosomes from infected and uninfected cells respectively (FIG. 3A). However, it is important to note that the results are drawn from a mixed population of exosomes and that individual exosomes will differ in the transcripts present and will contain only a subset of the total transcripts. This is likely also true for the miRNAs identified in exosomes.

A large number of transcripts detected in Rv exosomes encoded for ribosomal proteins and we could also detect transcripts encoding for RNA binding proteins such as rbed1, csde1, rbmxrt, tarbp2 etc. However, we also observed genes involved in MAPK signaling (tnfrsf1a, mapkapk2, phospholipaseA2, ly96) antigen presentation (cd14, cd40, cd80 and cd86) apoptosis (bcl2l1, irak2, nfkbia) and proteasome, (psmd13, psmb8, psmb9). From the total transcripts identified, 65 showed 2-fold or higher expression with a p value ≤0.05 in exosomes released from infected compared to uninfected cells. However, only 16 of these 65 transcripts showed greater than 2-fold higher expression in infected compared to uninfected RAW264.7 cells.

A subset of genes from the group of 65 upregulated transcripts were validated by SYBR Green based quantitative PCR including those previously characterized as functioning in immune responses such as prss15, slc15a3 and ncf4 (FIG. 3B). We also identified 69 transcripts that were down-regulated in exosomes from infected cells relative to uninfected cells including hmgb2, traf3, psmd3 and ctsf. Interestingly, we identified a subset of transcripts which appeared unique to each exosome population. A subset of the 46 transcripts present in exosomes from Mtb-infected cells included those involved in immune surveillance such as ccl21b, lcn2, traf1 and procr were further tested by PCR. As predicted from our array data, we did not detect these transcripts in exosomes from uninfected cells, confirming that they are absent or present at very low levels in this exosome population (FIG. 3C).

TABLE III

Unique Host transcripts identified from Rv infected exosomes.

| No. | Transcript ID | Description |
| --- | --- | --- |
| 1. | NM_008491 | 'Lcn2'; alt '24p3\|AW212229\|NGAL'; lipocalin 2 |
| 2. | XM_887648 | gene_name '1700045I11Rik'; alt '—'; RIKEN cDNA 1700045I11 |
| 3. | NM_009971 | 'Csf3'; alt 'Csfg\|G-CSF'; colony stimulating factor 3 (granulocyte) |
| 4. | XM_972624 | gene_name 'LOC664783'; alt '—'; similar to double homeobox 4c |
| 5. | NM_015809 | gene_name 'Krtap5-4'; alt '—'; keratin associated protein 5-4 |
| 6. | XM_898350 | gene_name 'LOC624422'; alt '—'; hypothetical LOC624422\| |
| 7. | NM_032541 | gene_name 'Hamp1'; alt 'Hamp\|Hepc\|Hepc1'; hepcidin antimicrobial peptide 1 |
| 8. | NM_011171 | gene_name 'Procr'; alt 'AI325044\|Ccca\|EPCR'; protein C receptor, endothelial |
| 9. | XM_972817 | gene_name 'LOC664808'; alt '—'; similar to transcription elongation factor B polypeptide 3C |
| 10. | XM_975981 | gene_name 'LOC665305'; alt '—'; hypothetical protein LOC665305 |
| 11. | XM_888852 | gene_name 'LOC624310'; alt '—'; hypothetical LOC624310 |
| 12. | XM_974918 | gene_name 'LOC665159'; alt '—'; similar to microtubule-associated protein 1A |
| 13. | XM_991636 | gene_name 'LOC667640'; alt '—'; similar to Transcription elongation factor B polypeptide 3 (RNA polymerase II transcription factor SIII subunit A1) (SIII p110) (Elongin A) (EloA) (Elongin 110 kDa subunit) |
| 14. | XM_356464 | gene_name 'Gm1153'; alt 'Tmf1'; gene model 1153, |
| 15. | NM_001024708 | gene_name 'LOC436177'; alt '—'; similar to Cadherin-11 precursor (Osteoblast-cadherin) (OB-cadherin) (OSF-4) |
| 16. | XM_897653 | gene_name 'LOC623296'; alt '—'; hypothetical LOC623296 |
| 17. | XM_990441 | gene_name 'LOC667415'; alt '—'; hypothetical protein LOC667415 |
| 18. | NM_009635 | gene_name 'Avil'; alt 'Advil\|DOC6'; advillin |
| 19. | XM_982314 | gene_name 'LOC666207'; alt '—'; similar to Spetex-2E protein |
| 20. | XM_888549 | gene_name 'LOC624023'; alt '—'; hypothetical LOC624023 |
| 21. | NM_001034869 | gene_name 'LOC245263'; alt '—'; similar to double homeobox, 4 |
| 22. | NM_183119 | gene_name '2410141K09Rik'; alt '—'; RIKEN cDNA 2410141K09 gene |
| 23. | XM_001001648 | gene_name 'LOC668470'; alt '—'; hypothetical protein LOC668470 |
| 24. | NM_175533 | gene_name '5830411N06Rik'; alt '—'; RIKEN cDNA 5830411N06 gene |
| 25. | XM_620264 | gene_name 'LOC545814'; alt '—'; sperm motility kinase 2-like |
| 26. | NM_172708 | gene_name 'A930013K19Rik'; alt 'MGC107606'; RIKEN cDNA A930013K19 gene |

TABLE III-continued

Unique Host transcripts identified from Rv infected exosomes.

| No. | Transcript ID | Description |
|---|---|---|
| 27. | NM_015783 | gene_name 'Isg15'; alt '15 kDa\|G1p2\|IGI15\|IP17\|Irfp\|MGC103144\|MGC130321\|UCRP'; ISG15 ubiquitin-like modifier |
| 28. | XM_894566 | gene_name '2810032E02Rik'; alt 'MGC118314'; RIKEN cDNA 2810032E02 gene |
| 29. | XM_902425 | gene_name 'Gm88'; alt '—'; gene model 88, |
| 30. | NM_001025379 | gene_name 'Sema3g'; alt 'AK129018'; sema domain, immunoglobulin domain (Ig), short basic domain, secreted, (semaphorin) 3G |
| 31. | NM_033616 | gene_name 'Csprs'; alt 'D1Lub1\|HSR\|MGC29132'; component of Sp100-rs |
| 32. | NM_008218 | gene_name 'Hba-a1'; alt 'Hba1'; hemoglobin alpha, adult chain 1\| |
| 33. | XM_886613 | gene_name 'LOC622201'; alt '—'; similar to reproductive homeobox on X chromosome 2 |
| 34. | NM_145440 | gene_name 'Uts2r'; alt 'Gpr14\|UTR\|UTR2'; urotensin 2 receptor |
| 35. | XM_486090 | gene_name 'Nkx6-3'; alt '9130417I07Rik\|Nkx6.3'; NK6 transcription factor related, locus 3 |
| 36. | NM_001033128 | gene_name 'Bbs1'; alt 'AI451249\|D19Ertd609e'; Bardet-Biedl syndrome 1 homolog (human) |
| 37. | NM_011124 | gene_name 'Ccl21b'; alt '6CKBAC2\|6Ckine\|ALP\|AW987545\|CKb9\|MGC107632\|SLC\|Scya21\|Scya21b\|Tca4\|plt'; chemokine (C-C motif) ligand 21b |
| 38. | XM_892362 | gene_name 'LOC627670'; alt '—'; similar to coiled-coil-helix-coiled-coil-helix domain containing 2 |
| 39. | XM_001003727 | gene_name 'LOC668807'; alt '—'; hypothetical protein LOC668807 |
| 40. | XM_886726 | gene_name 'LOC622301'; alt '—'; similar to reproductive homeobox on X chromosome 2 |
| 41. | NM_028362 | gene_name '2410018L13Rik'; alt '2810480C08Rik'; RIKEN cDNA 2410018L13 gene |
| 42. | NM_009421 | gene_name 'Traf1'; alt '4732496E14Rik'; Tnf receptor-associated factor 1 |
| 43. | XM_974176 | gene_name 'LOC665048'; alt '—'; similar to ribosomal protein S8 |
| 44. | NM_010487 | gene_name 'Elavl3'; alt 'Huc\|PLE21\|mHuC'; ELAV (embryonic lethal, abnormal vision, Drosophila)-like 3 (Hu antigen C) |
| 45. | XM_128114 | gene_name '4930415O20Rik'; alt '—'; RIKEN cDNA 4930415O20 gene |
| 46. | NM_009824 | gene_name 'Cbfa2t3h'; alt 'A630044F12Rik\|ETO-2\|MTGR2'; core-binding factor, runt domain, alpha subunit 2, translocated to, 3 homolog (human) |

To determine whether selective incorporation of these transcripts into exosomes relates to their enrichment in host cells following a mycobacterial infection, we analyzed the expression patterns of these transcripts in Mtb-infected cells compared to uninfected cells. We found that most transcripts were enriched in macrophages infected with Mtb compared to uninfected cells suggesting that the presence of these unique transcripts in exosomes stem, at least in part, from their higher expression in infected cells (data not shown). A KEGG Pathway analysis was undertaken on the total transcripts identified in exosomes. We observed a few functional pathways which were specific to exosomes from infected or uninfected cells but the majority of pathways were defined in both exosome populations including regulation of actin cytoskeleton, TLR signaling and MAPK signaling among others. For the 46 unique transcripts identified in exosomes from infected cells, only the cytokine-cytokine receptor interaction emerged as significant. For the 65 transcripts that were upregulated in exosomes from infected compared to uninfected cells, the pathways identified included proteasome, Ag processing and presentation and Systemic lupus erythematosus.

Figure 4:
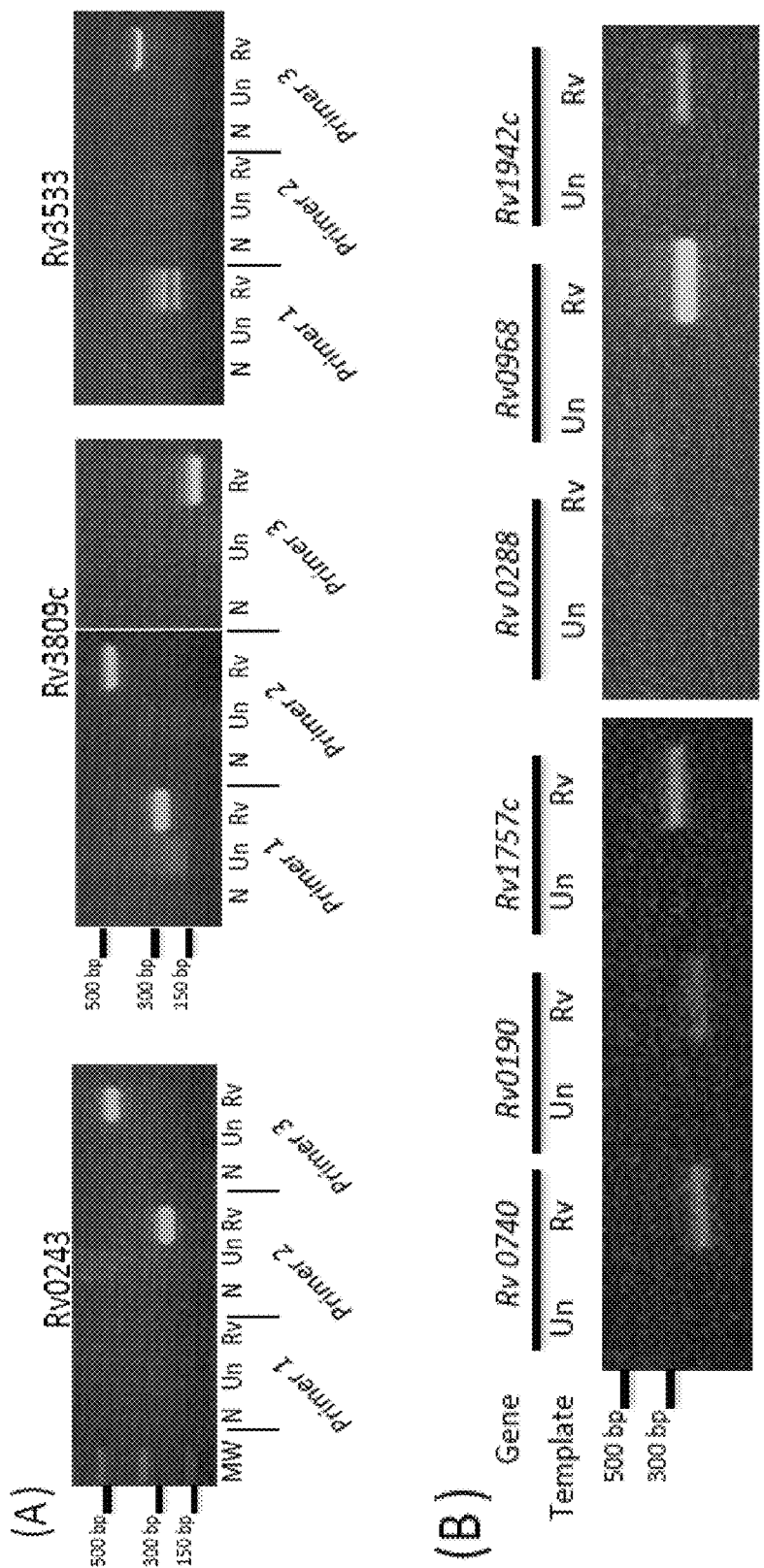
FIG. 4 illustrates exosomes released from Mtb-infected macrophages contain mycobacterial RNA. Multiple sets of primers were designed for selected mycobacterial transcripts that were identified in sequencing of the exosome small RNA library. PCR amplifications were performed for each primer pair to amplify different regions of each transcript (A). Exosomal RNA was reverse transcribed to double stranded cDNA, labeled with Cy3 and hybridized to whole Mtb genome arrays. Selected mycobacterial transcripts identified in the gene expression analysis were validated by PCR (B).

Exosomes Released from *M. tuberculosis* Infected Macrophages Contain Mycobacterial Transcripts A BLAST analysis against the whole Mtb transcriptome was performed using the sequence data from the small RNA library. We identified mycobacterial transcripts Rv3809c, Rv3533, Rv0243, Rv1101c and Rv2024c multiple times in the RNA library when using exosomes isolated from infected macrophages. Although our sequence data indicated that exosomes contain fragments of these mycobacterial genes, the length of the transcripts were unclear as we only selected for small RNA fragments when generating the library. Therefore, we designed multiple primers for Rv3809, Rv3533 and Rv0243 to provide maximum coverage for each gene. RNA was isolated from independent exosome preparations and converted to cDNA which was used as template for the PCR. We detected PCR products for each of these three mycobacterial transcripts. No products were identified when using the cDNA generated from exosomes released from uninfected cells (FIG. 4A). Although we could detect products for 2 or 3 primer sets for each transcript, we could not detect full length transcripts using primers that extend the whole gene suggesting that only fragments of mycobacterial transcripts get incorporated into exosomes released from Mtb-infected macrophages.

To detect other potential mycobacterial transcripts in exosomes released from infected cells, total RNA was converted to ds cDNA, labeled with Cy3 and hybridized onto a custom whole MTB genome array. RNA from uninfected exosomes was used as negative control and Mtb RNA as a positive control. These gene expression studies identified an additional 13 mycobacterial transcripts in exosomes from infected macrophages. Independent preparations of exosomal RNA were used to validate the gene expression results by RT-PCR. These results confirmed the presences of 9 of the 13 mycobacterial transcripts which included Rv0740, Rv0288, Rv1344, Rv0968, Rv1942c, Rv0664, Rv0190, Rv1757c and Rv1369c. A few representative transcripts are shown in FIG. 4B. As expected, the mycobacterial transcripts were not detected in exosomes released from uninfected macrophages.

Exosomal RNA can be Transferred to Recipient Cells

Figure 5:
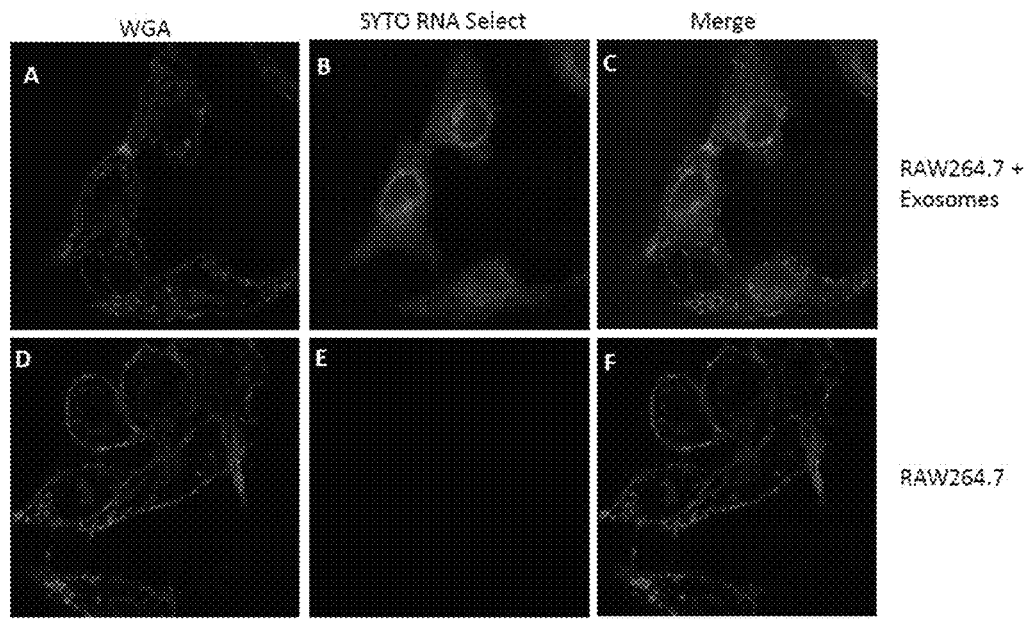
FIG. 5 illustrates exosomal RNA can be transferred to recipient macrophages. RAW264.7 cells were treated with Alexa Fluor 594-labeled Wheat Germ Agglutinin (WGA) to visualize cell membranes. Purified exosomes were labeled with the SYTO Select RNA stain and these labeled exosomes were added to RAW264.7 cells or left untreated. The monolayers were washed and the uptake of exosomal RNA was visualized using a BioRad MRC 1024 Scanning Confocal coupled to a Nikon Diaphot 200 microscope using LaserSharp 2000 acquisition software. The images were acquired at 40× with 2× digital zoom with x, y dimensions of 0.24 µm per pixel and the images were processed using Image J software. Shown is a representative picture from two independent experiments.

To evaluate whether RNA from exosomes can be transferred to uninfected macrophages, purified exosomes were labeled with SYTO RNA select stain and added to RAW 264.7 cells that were stained with wheat germ agglutinin (WGA) to visualize cell membranes. As observed by fluorescent microscopy, the RNA in exosomes was transferred to recipient macrophages and appeared primarily cytoplasmic (FIG. 5).

Exosomal RNA can be Translated to Protein Upon Delivery to Recipient Cells

Figure 6:
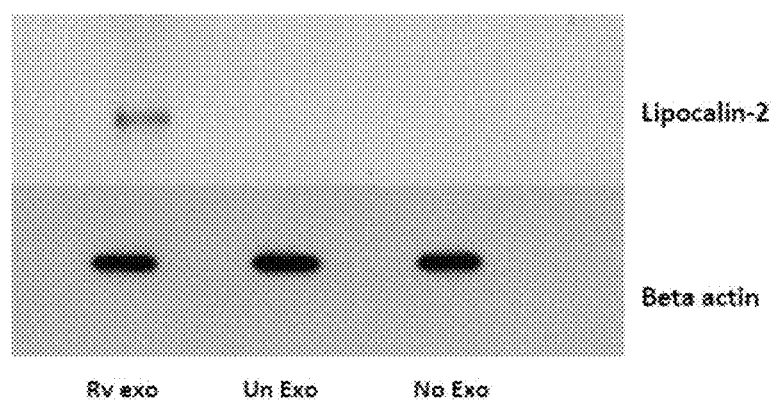
FIG. 6 illustrates exosomal RNA leads to synthesis of protein upon delivery to recipient cells. PMA differentiated THP-1 cells were treated with exosomes derived from Mtb infected or uninfected RAW264.7 macrophages or left untreated. After 24 hours, cells were harvested, lysed in RIPA buffer and probed with mouse lipocalin-2/NGAL antibody or rabbit monoclonal antibody for beta actin.

In view of the transfer of exosomal RNA to recipient cells, we evaluated whether exosomal RNA delivered to recipient cells was translated. We targeted the mRNA encoding mouse lipocalin-2 since it was detected exclusively in exosomes derived from Mtb infected macrophages but not from uninfected macrophages. Further, lipocalin-2 is known to inhibit mycobacterial growth in vitro through sequestration of iron uptake implicating its role in the mycobacterial innate immune response. Human THP-1 cells were incubated with mouse exosomes derived from Mtb infected cells or uninfected cells for 4 hours and the monolayers were washed to remove any remaining extracellular exosomes. Untreated THP-1 cells were used as a control. The cells were incubated for 24 hours, lysed and probed for mouse lipocalin-2 protein expression by western blot. As shown in FIG. 6, we observed the expression of murine lipocalin-2 upon treatment of human THP-1 cells with mouse exosomes from infected cells. No lipocalin-2 was observed in THP-1 cells treated with exosomes from uninfected cells or in control untreated THP-1 cells. Our results indicate that exosomal mRNA can be transferred into recipient cells and translated into protein.

Exosomal RNA Induces a Pro-inflammatory Response in Recipient Cells

As our data supports the transfer of exosomal RNA to recipient macrophages, we next evaluated the macrophage's biological response to this RNA. Exosomal RNA was transfected into RAW264.7 cells using the Hiperfect transfection reagent which is a mixture of cationic and neutral lipids and facilitates the cellular uptake of RNA. The RNA dosage corresponded to approximately 50 exosomes per cell in our experiments. 24 hours post transfection, the cell culture supernatants were profiled for 40 different cytokine and chemokines using a mouse cytokine array. As a control, some cells were treated with Hiperfect alone. Exosomal RNA from both uninfected and Mtb-infected macrophages induced significantly higher levels of sICAM-1, RANTES and I-TAC compared to untreated cells or cells treated with the Hiperfect transfection reagent. However, only RNA isolated from exosomes released by infected cells induced a significant increase in the secretion of CCl2, MIP-2, TNF-α and IL-1ra by RAW264.7 macrophages compared to resting cells or cells treated with Hiperfect alone (FIG. 6A and FIG. 6B).

Since mycobacterial transcripts were detected in the exosomal RNA and previous reports indicate that mycobacterial RNA can induce apoptosis in human macrophages we addressed the possibility that the RNA from exosomes derived from infected cells could induce apoptosis in recipient cells. As shown in FIG. 6C transfection of naïve cells with this exosomal RNA resulted in elevated levels of phosphatidyl serine on the outer leaflet of the plasma membrane as defined by annexin-V staining. Increased phosphatidyl serine exposure is associated with early events in apoptosis. Quantitation of the number of annexin-V positive cells+/−transfection with exosomal RNA is shown in FIG. 6D.

Figure 7:
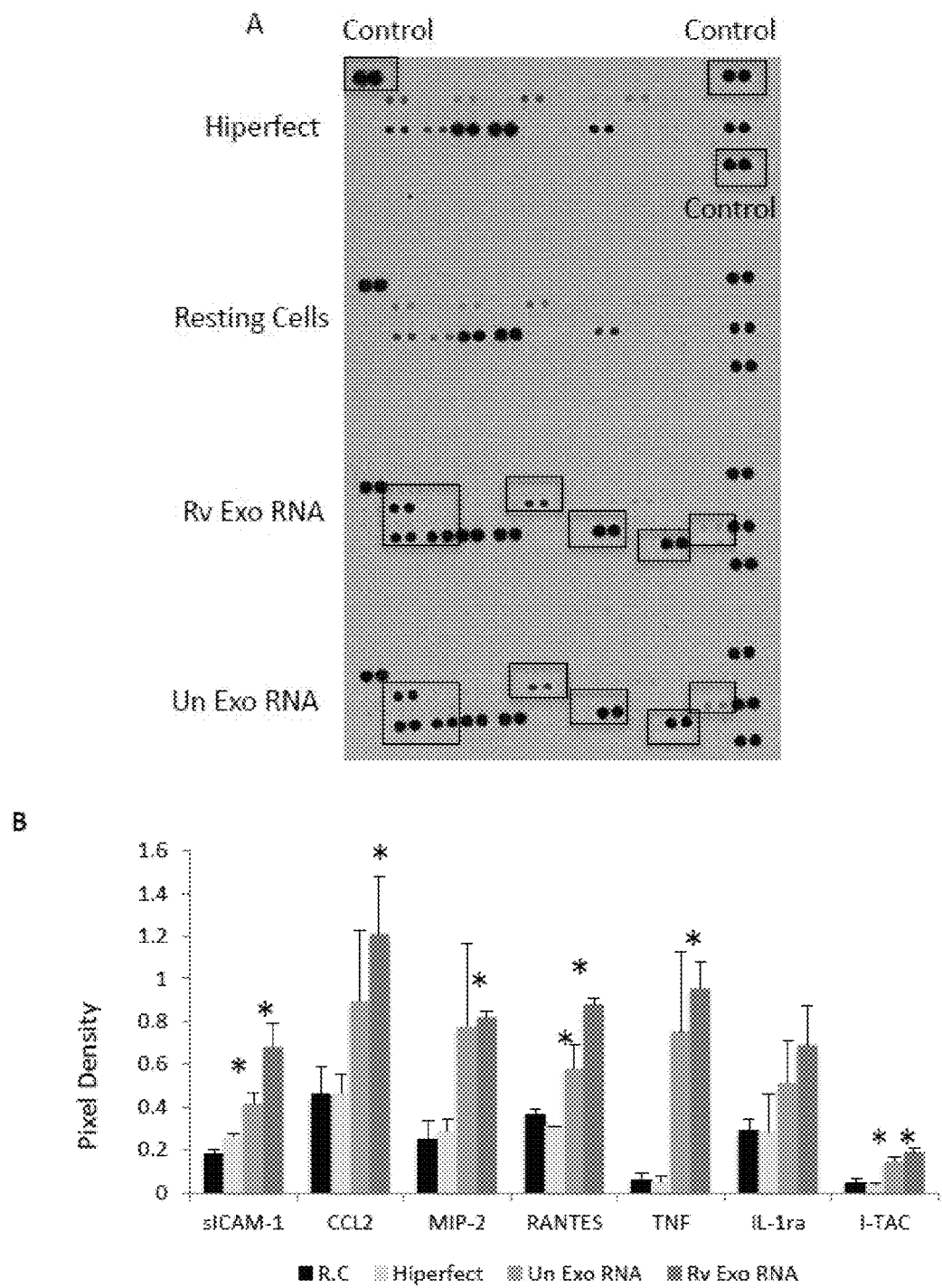
FIG. 7 illustrates transfection of recipient cells with exosomal RNA stimulates cytokine and chemokine secretion and induces significant apoptosis. RNA was isolated from exosomes released from uninfected or Mtb infected RAW264.7 macrophages. 250 ng of RNA was mixed with 3 µl of Hiperfect transfection reagent and added to RAW264.7 macrophages. Untreated macrophages or macrophages treated with Hiperfect reagent alone were used as controls. Following incubation in growth media for 24 hours, cell culture supernatants were harvested and probed for the presence of cytokines or chemokines using a Mouse Cytokine Antibody Array Panel (A). Pixel densities for spots corresponding to differentially expressed proteins were defined using Image J software and plotted (B). In separate experiments, cells were stained with FITC-Annexin V and fixed with 2% paraformaldehyde. FITC-labeled cells were visualized on a confocal microscope (C) and the percentage of Annexin-V positive cells defined by visual counting (D). Graphs results are a combination of two independent experiments +SD. * indicates a P<0.5 compared to untreated cells.
Figure 7:
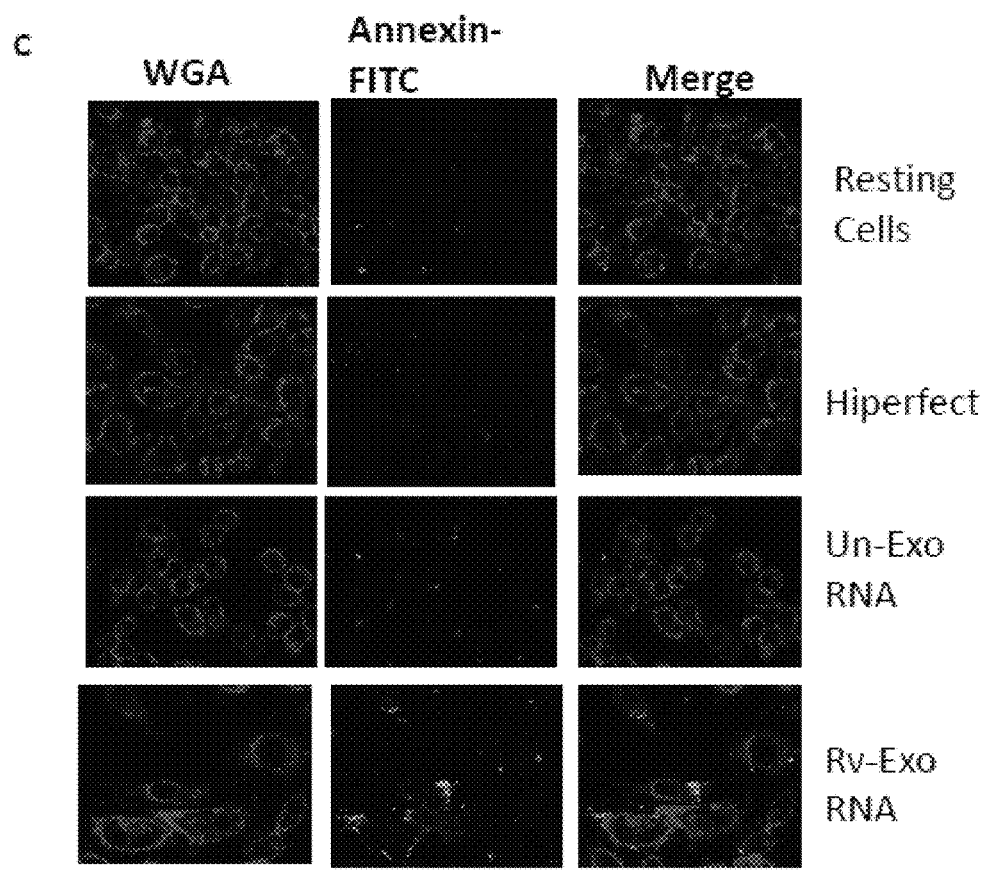
Figure 7:
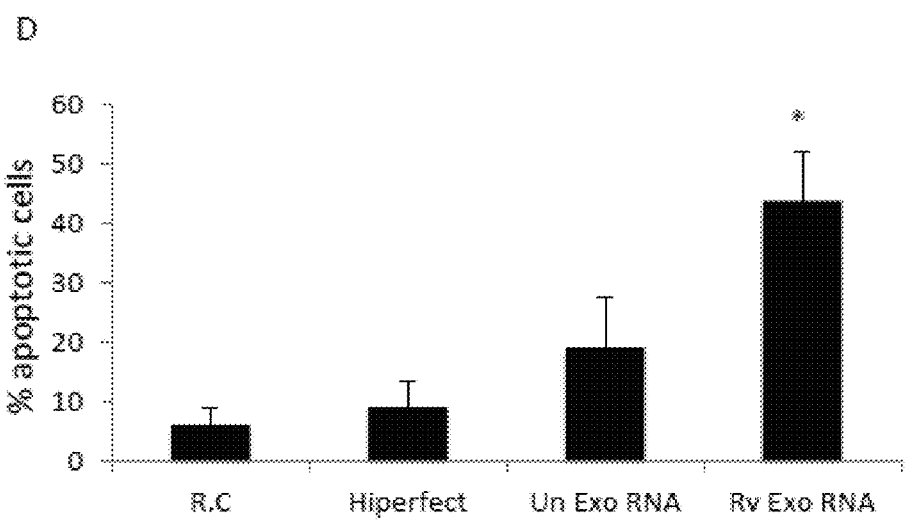
Figure 8:
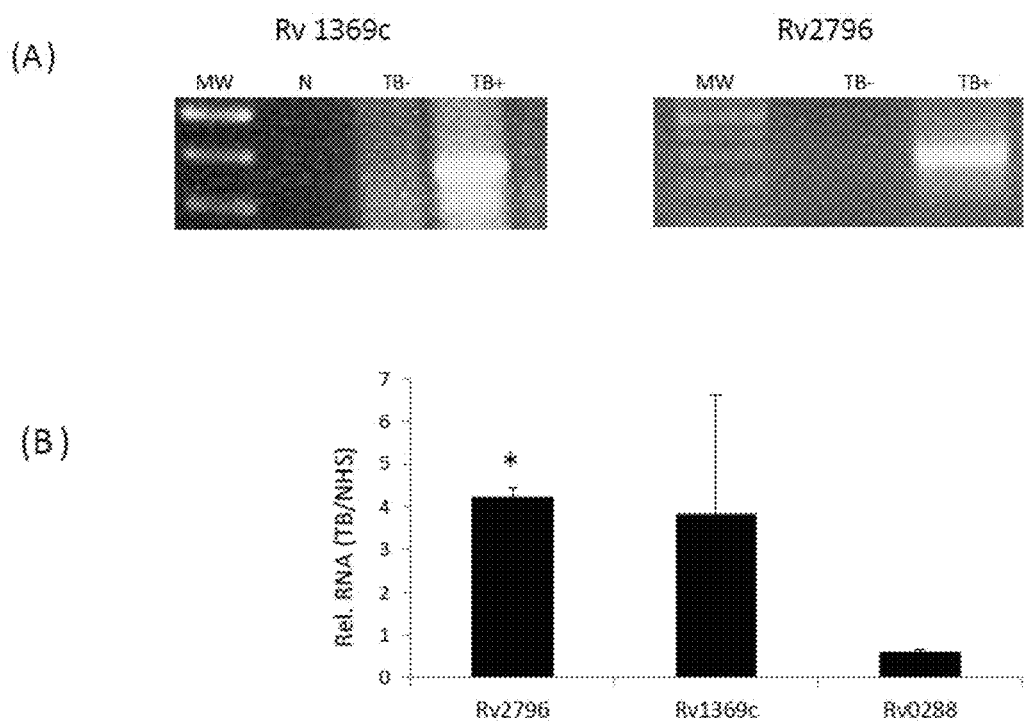
FIG. 8 illustrates RNA isolated from EVs derived from serum of TB-infected individuals contains mycobacterial transcripts. RNA was isolated from exosomes derived from the serum of culture-positive TB patients and from healthy uninfected control subjects. The RNA was initially amplified and then reverse transcribed to double stranded cDNA, labeled with Cy3 and hybridized to whole Mtb genome arrays. The Mtb transcripts that were identified in the array analysis were selected for validation by RT-PCR (A) and SYBR Green based qRT-PCR (B). N; no template control, Un; exosomes from uninfected cells, Rv; exosomes from infected cells, TB–; exosomes isolated from non-TB, healthy control serum, TB+; exosomes isolated from TB patient serum. Results are from the average of two separate experiments +SD.

Mycobacterial Transcripts are Present in Extracellular Vesicles (EVs) Derived from Serum of Human TB Patients With the detection of mycobacterial transcripts in exosomes released from Mtb-infected macrophages, we explored the possibility of detecting Mtb transcripts in exosomes isolated from human TB patient serum. RNA was isolated from extracellular vesicles purified from the serum of culture positive TB patients or from a healthy control. Since we were limited in the amount of human serum and therefore vesicles, we pre-amplified the exosomal RNA using a WTA amplification kit to obtain sufficient quantity of cDNA for hybridization onto the whole Mtb genome arrays. From the hybridization experiments we putatively identified five mycobacterial transcripts in exosomes from TB patients. To further evaluate whether the genes defined in the array experiments were present in TB patient exosomes, primers were designed for each of these mycobacterial transcripts and the cDNA, produced from pre-amplified RNA, was used as a template for PCR. We confirmed that Rv2796 and Rv1369c were present in serum exosomes from TB infected individuals as shown by PCR and SYBR Green based qPCR (FIG. 7A and FIG. 7B).

Discussion. Recent studies have shown that exosomes, as vehicles of intercellular communication, not only transport proteins and lipids, but also biologically active RNA. The RNA encapsulated in exosomes is termed "exosomal shuttle RNA" (esRNA) and consists of functional miRNA and mRNA that can be transferred to recipient cells and modulate their transcriptome. Exosomal RNA has been studied in diverse fields such as cell biology, immunology, cancer biology, neurobiology and has been characterized in several cell types including mast cells, T and B cell lines, bone marrow derived dendritic cell, macrophages and carcinoma cell lines. These studies indicate that exosomes provide a natural delivery system for RNA both in vitro and in vivo and highlight the potential use of exosomal RNA as molecular biomarkers against several diseases. However, the role of exosomes in transporting genetic material, specifically RNA in a background of a bacterial infection has not been undertaken. We addressed this question in the context of a mycobacterial infection. In the present study, we have defined the RNA content of exosomes released from murine RAW264.7 macrophages following infection with Mtb and showed these exosomes to contain miRNA, mRNA as well as mycobacterial transcripts. Further, the detection of mycobacterial transcripts in exosomes was not limited to an in vitro infection as extracellular vesicles derived from TB patient serum also contained TB transcripts.

The role of miRNAs in responding to bacterial infections is poorly understood. The miRNAs could be involved in regulating gene expression for pathways that are important in the immune response to pathogens. Differences in circulating miRNAs in serum of TB patients compared to controls have been observed and these differences may provide signatures to distinguish active from latent TB. Although the authors did not specifically look at exosomes, it is known that most miRNAs in human serum or saliva are encapsulated in exosomes allowing for increased stability of the RNA. Recently, exosome-enclosed miRNAs in exhaled breath have been suggested as potential biomarkers for patients with pulmonary diseases such as tuberculosis.

In our initial experiments, we focused on the miRNAs present in exosomes released from Mtb-infected macrophages and how this compares to exosomes from uninfected cells. To explore this question, we adopted a sequencing approach to identify the miRNAs in exosomes. Although we identified a subset of miRNAs that were specific to exosomes from infected cells, most miRNAs identified were present in exosomes from both infected and uninfected macrophages, suggesting a general conservation in the trafficking and incorporation of miRNAs into exosomes. In total, we identified 57 miRNAs in exosomes released from infected macrophages including Mmu 223 and 486-5p which belong to the cohort of differentially expressed miRNAs in the serum of TB patients. Previous studies have shown that miRNA 99b is highly up-regulated in *M. tuberculosis* infected dendritic cells (DCs) and it targets TNF-α and TNFRSF-4 receptor gene transcripts and that downregulation of this miRNA leads to a significant loss in bacterial survival in DCs. Mycobacterial secreted protein ESAT6 is also a known effector of miR-155 whose upregulation following an Mtb infection modulates the expression of a subset of proteins that benefit the establishment of an infection.

These results suggest that cellular miRNAs which are up-regulated following infection with Mtb may provide a mechanism of immune evasion by the pathogen. Surprisingly we found in our quantitative RT-PCR studies that the level of these as well as other miRNAs was significantly diminished in exosomes released from Mtb-infected compared to uninfected cells. The identified miRNAs were involved in various pathways including Calcium signaling, MAPK signaling, Natural killer cell mediated cytotoxicity, and Jak-STAT signaling all of which are involved in the immune response to infection. This difference in miRNAs between the exosome from infected and uninfected cells was not reflected in the concentration observed in whole cells. However, we only defined their cellular concentration 72 hours post-infection and therefore it is unclear how they compared at earlier time points.

The mechanism for miRNA incorporation into exosomes is still being defined. However, a recent study indicates that the RNA binding protein Heterogeneous Nuclear Ribonucleoprotein A2B1 (hnRNPA2B1) can bind a specific subset of miRNAs through their EXOmotifs and control their loading into exosomes. This suggests that the repertoire of RNA binding proteins present within an exosome may affect which miRNAs are trafficked and incorporated into exosomes. Interestingly, we found an increased expression of Annexin II in exosomes released from infected cells compared to uninfected cells (data not shown). Recently Annexin II has been identified as a novel RNA binding protein that binds directly to both ribonucleotide homopolymers and human c-myc RNA and it has been hypothesized to be involved in the recruitment of appropriate cellular and/or viral components to generate HCV-RNA-containing exosomes.

This study also defined the mRNA signatures within exosomes and found distinct subsets of transcripts enriched in each group suggesting selective incorporation of host mRNA into exosomes. Analysis of the data identified a unique group of transcripts present only in exosomes from infected cells which included genes such as traf, lcn2 that are known to play an important role in innate immunity. Several transcripts were also identified that were present at significantly higher or lower concentration in exosomes from infected compared to uninfected cells. A GO analysis indicated that the affected pathways included cytokine-cytokine receptor interaction, proteasome, antigen processing and presentation and systemic lupus erythmatosus. The observation that within exosomes released from infected cells we observe diminished levels of miRNAs which block translation of genes involved in the host immune response while genes involved in promoting inflammation show relatively higher concentration suggest that the RNA content of these exosomes is primed to stimulate the host immune response to a mycobacterial infection. Since exosomes exert their affect beyond the infected cell, it is possible that the export of these RNA molecules work in concert with cytokines and other factors to stimulate the immune response against invading pathogens. Future studies are needed to understand the mechanisms that determine incorporation of select mRNAs into exosomes.

Unexpectedly we detected mycobacterial transcripts in exosomes derived from Mtb-infected macrophages. We identified the mycobacterial transcripts through sequencing of the small RNA library as well as in our expression analysis using Mtb whole genome arrays. Previous studies have shown the presence of viral trans-activator response element (TAR) RNA in exosomes isolated from cell culture supernatants of HIV-1 infected cells and from patient sera. This TAR miRNA was not associated in the Ago2 complexes outside the exosomes but was enclosed within exosomes. Epstein Barr virus encoded miRNAs have also been shown to be secreted by EBV infected B cells via exosomes. Beyond viral RNA, our study is the first to show the presence of pathogen associated RNA in exosomes released from infected cells. How mycobacterial RNA is incorporated into exosomes is presently unclear. However, previous reports have shown that mycobacterial DNA gains access to cytosolic receptors likely through perforation of the phagosome membrane mediated by the ESX-1 secretion system. Also, previous studies have shown SecA2-mediated secretion of bacterial nucleic acids by *Listeria monocytogenes* that enables infected macrophages to detect viable bacteria in cytosol via immune sensory receptors RIG-I, MDA5 and STING. There are likely additional mechanisms that contribute to the presence of prokaryote RNA in cytosol of infected cells. These include leakage of bacterial debris that contains nucleic acids from phagosomal compartments autolysis within the cytosolic compartment or nucleic acid release from viable bacteria in the cytosol.

Since exosomes released from Mtb infected macrophages contain a distinct repertoire of microRNAs, mRNAs as well as pathogen derived mycobacterial RNA, we hypothesized that the exosomal RNA would elicit a unique host response upon its delivery to recipient cells. Our study indicated that exosomal RNA can be transferred to recipient RAW264.7 cells and that the mRNA for mouse lipocalin-2 present in exosomes from infected cells could be translated to protein upon delivery to human THP-1 cells. These results show the functionality of the RNA encapsulated in exosomes Since it was necessary to distinguish the activity of the exosomal RNA in modulating the host immune response from that played by the pathogen associated molecular patterns (PAMPs), also present in exosomes released from infected macrophages, it was necessary to purify the exosomal RNA away from the other exosome components.

The purified RNA was transfected into naïve RAW264.7 cells and the treated cells evaluated for expression of various cytokines and chemokines. We observed certain commonalities in the cellular response when using exosomal RNA from infected and uninfected cells. However, exosomal RNA from infected cells was more potent in not only inducing higher secretion of TNF-α, MIP-2 and CCL2 but also in driving apoptosis. At present, it is unclear if the increased apoptosis is due to the presences of mycobacterial RNA in these exosomes. Nevertheless, our results indicate that specific host- or mycobacterial-derived RNA molecules present in exosomes released from infected cells could contribute to a pro-inflammatory response and apoptotic signals in cells recruited to the site of an Mtb infection.

In conclusion, our study shows that Mtb-infected macrophages secrete exosomes that contain a unique subset of host miRNAs and mRNA as well as mycobacterial RNA. This unique composition leads to a differential response by the recipient cells. We hypothesize that the host immune response would benefit from the exosomes released from infected macrophages due to the specific composition of host miRNAs and mRNAs; however, a test of this hypothesis awaits further study. Finally, we also report the detection of mycobacterial RNA in exosomes isolated from TB patient serum. These results point to the potential use of exosomal RNA in TB diagnostics. This is the first study to characterize the RNA content of exosomes in the context of a bacterial infection and adds an additional layer of complexity to the function of exosomes during an Mtb infection.

Materials & Methods. Ethic Statement for use of human material: Only publicly available, de-identified or unidentified serum samples were used for this project and the Notre Dame Institutional review board under protocol #13-09-1221 gave exempt status to the isolation of exosomes from human serum as performed in this study.

Exosome Isolation: Exosomes were isolated from cell culture supernatants of uninfected or *M. tuberculosis* (H37Rv) infected macrophages as previously described. Serum of TB patients was kindly provided by the foundation of New and Innovative Diagnostics (FIND), UCSF and included serum from HIV positive and HIV negative TB patients. Extracellular vesicles were isolated from a total of 4.8 ml of TB patient serum and 8 ml of serum obtained from a healthy volunteer by successive centrifugation steps. Briefly, the serum was passed through 0.4 μm filter and centrifuged at 1,500×g for 15 minutes followed by 17,000×g for 30 minutes. The supernatant was finally centrifuged at 100,000×g for 2 hours to pellet the extracellular vesicles.

RNA Isolation & cDNA Synthesis: RNA was isolated from exosomes derived from cell culture supernatants or human serum using MirVANA kit (Ambion) following manufacturer's instructions. Prior to RNA isolation exosomes were treated with RNAse A at 10 μg/ml at 37° C. for 30 minutes to confine the analysis to RNA encapsulated within the exosomes. Exosomes were also treated with DNAse1 (Invitrogen) following manufacturer's instructions. The RNA isolated from serum exosomes was pre-amplified using Whole Transcriptome Amplification kit WTA-2 (Sigma).

Construction of Small RNA Libraries: The RNA was size fractionated on a 15% tris-borate-EDTA (TBE) urea polyacrylamide gel (Biorad) and small RNA libraries were constructed (Morin et al., Genome Res. 2008; 18: 610-621). The concentration of cDNA libraries for small RNA were determined with a fluorescence based quantitation method (PicoGreen) and the samples were run on Roche 454 Genome Sequencer FLX instrument following manufacturer's instructions. The raw reads were filtered to eliminate adaptor and primer sequences and the sequences in fasta format were run against the mature mouse miRNA sequences available in miRBase using BLAST software under linux operating system. MicroRNAs were identified using E value 0.01 or 1.

qPCR Validation of miRNAs: Total RNA from exosomes was polyadenylated and reverse transcribed to cDNA using qScript miRNA cDNA synthesis kit (Quanta Biosciences). QPCR was performed using PerfeCTa SYBR Green SuperMix and samples were run on AB7500 Fast Cycler following manufacturer's instructions. The relative miRNA expression was normalized to the endogenous reference gene and was quantitated using the comparative $C_t$ method with the formula $2^{-\Delta\Delta C_T}$.

Gene Expression Studies: Total RNA from exosomes or from RAW264.7 cells were converted to double stranded cDNA using Super Script ds cDNA synthesis kit (Invitrogen), labeled and hybridized onto Nimblegen arrays (mouse or *M. tuberculosis* genomes) as previously described (Singh et al., PloS ONE 2011; 6: e18564.). Pathway analysis was performed with the Pathway-Express program of the Ontotools Suite.

SYTO RNA Select Staining of Exosomes: Purified exosomes were labeled with SYTO RNA Select green fluorescent stain (Molecular Probes) following the manufacturer's instructions and excessive stain was washed from exosomes by centrifugation in 1×PBS. The cell monolayers ($1\times10^5$/well) were treated with labeled exosomes (25 μg/well) for 2 hours. The monolayers were washed with 1×PBS and the cells were stained with Alexa Flour-594-labeled Wheat Germ Agglutinin stain per manufacturer's instructions. Images were acquired on a BioRad MRC 1024 Scanning Confocal coupled to a Nikon Diaphot 200 microscope using LaserSharp 2000 acquisition software. The settings included laser power (30%), Iris diameter in Airy units (2.5), gain (1386) and an offset (24) with PMT off. The images were acquired at 40× with 2× digital zoom with x, y dimensions of 0.24 μm per pixel and the images were processed using Image J software.

In Vivo Translation: Human THP-1 cells ($1\times10^6$) were differentiated with 20 ng/ml PMA for 48 hours. The monolayers were washed with PBS and incubated in complete RPMI media for an additional 24 hours. Exosomes (125 μg) derived from Mtb infected or uninfected mouse RAW264.7 macrophages were added to the cells or the cells were left untreated for 4 hours. The cells were subsequently washed to remove remaining exosomes and fresh culture media was added. 24 hours later cells were lysed in RIPA buffer and probed for mouse lipocalin-2 expression using monoclonal Mouse Lipocalin-2/NGAL antibody (R&D Systems) which does not cross react with human Lipocalin 2. Samples were also probed with Rabbit monoclonal antibody for beta actin (Cell Signaling) as a loading control.

Transfections: RAW264.7 macrophages ($2\times10^5$ cells per well) were seeded in a 24 well plate in DMEM complete growth medium. 250 ng of exosomal RNA was mixed with 3 μl of Hiperfect transfection reagent (Qiagen) and added drop wise to the cells following manufacturer's instructions. Resting macrophages or macrophages treated with the transfection reagent Hiperfect alone were used as controls. Following incubation in normal growth conditions for 24 hours, the cell culture supernatants were harvested and tested for presence of cytokines and chemokines using Mouse Cytokine Array Panel A (R&D Systems) following manufacturer's instructions. In separate experiments, RAW264.7 macrophages were seeded on coverslips and transfected with exosomal RNA as described above. The cells were stained with FITC conjugated Annexin V (BioLegend) following manufacturer's instructions and fixed with 2% paraformaldehyde. The cells were visualized on a confocal microscope and the percentage of apoptotic cells was determined by counting cells in 10 independent fields for each treatment.

Statistical Analyses: Data was analyzed by a one-tailed or paired Student's t test. Statistical significance was assumed at $p\leq0.05$. Each experiment was conducted 2 or 3 times and error bars represent standard deviation values.

Example 2. Identification of Extracellular Vesicle RNA Biomarkers

1. Mouse Infection

Wild type C57BL/6 mice were retro-orbitally infected with $1\times10^6$ wild type *Mycobacterium tuberculosis* (Mtb)

H37Rv in the biosafety level three laboratory (TB sample). A second group of mice injected with PBS was used as a control (Control).

2. Serum Preparation

Two weeks after infection, mouse blood was harvested by cardiac puncture and serum was prepared using BD microtainer serum separator tubes in the biosafety level 3 laboratory.

3. Vesicle Preparation a) Prepared serum was then passed through a 0.22 μm spring filter in the biosafety level three laboratory. b) Serum was centrifuged at 10,000×g, 4° C., 60 min, to remove microvesicles and other larger vesicles. c) The supernatant was transferred into a fresh ultracentrifuge tube and ultracentrifuged at 100,000×g, 4° C., 60 min in Beckman Benchtop Ultracentrifuge. d) The pellet was washed in 1×PBS twice and again centrifuged at 100,000×g, 4° C., 60 min. e) Final pellet was resuspended in 50 μl of 1×PBS, and stored at −80° C. freezer (ready for RNA extraction).

4. RNA Preparation a) Exosomes were sequentially treated with RNase A and DNase I to remove any RNA or DNA not present within the exosome (i.e. attached to outside surface) RNase A (Invitrogen PureLink Cat#12091-021) at 10 μg/mL at 37° C. for 30 min. DNaseI (Invitrogen, #18068-015), incubate tube(s) for 15 min at room temperature. b) Exosomal RNA was extracted using mirVana™ miRNA Isolation Kit (Ambion, Cat. AM1560) according to the manufacturer's protocol. c) RNA concentration and quality was determined by Agilent Bioanalyzer RNA 6000 pico.

5. RNA Sequencing (Genomics and Bioinformatics Core Facility, University of Notre Dame)

a) Small RNA libraries were constructed using NEBNext® Multiplex Small RNA Library Prep Set for Illumina® (Set 1) following the manufacturer's handbook. b) The quality and concentration of cDNA libraries for small RNAs was determined using Bioanalyzer DNA 1000 chips (Aligent) and Qubit DNA high sensitivity assay (Invitrogen), respectively. c) The samples were applied to Illumina MiSeq Desktop Sequencer.

6. Bioinformatic Analysis a) The raw Illumina sequence data was verified with the quality control program, FastQC, to eliminate any low-quality data. b) The adaptor of sequence was removed using the read trimming tool, Trimmomatic, with the single end mode. c) The trimmed sequence was further verified with the quality control program, FastQC, to eliminate any low-quality data. d) Mapping of reads to Mtb genome using bwa-0.7.12, and match sites identical to reads were retrieved. e) Identify the unique mapping site in TB vs Control sample (Bash Commands in Linux). f) Verify match sites using IGV (Integrative Genomics Viewer) manually. g) Identify Mtb ORF in which the match site is located (Bash Commands in Linux). Sixteen Mtb gene candidates were finally determined (Rv0169, Rv0170, Rv0347, Rv0434, Rv0453, Rv0517, Rv0586, Rv0668, Rv0730, Rv0907, Rv1609, Rv1629, Rv2001, Rv2100, Rv2395, Rv3871).

7. Mtb RNA Verification by RT-PCR a) Exosomal cDNA library was prepared using qScript miRNA cDNA synthesis kit (Quanta Biosciences, #95107-025) following the manufacturer's protocol. b) Six gene candidates (Rv0170, Rv0730, Rv0453, Rv0586, Rv0668, Rv1629) were verified using gene-specific primers and GoTaq® Green Master Mix (Promega, M7122). c) PCR products were analyzed by 2% agarose gel electrophoresis.

8. Mtb RNA Verification by DNA Sequencing.

a.) PCR products were then purified by Qiagen Gel Extraction kit (Cat. 28704) and then the DNA sequence was determined by DNA sequencing.

Example 3. Detection of *Mycobacterium* RNA in Exosomes

Figure 9:
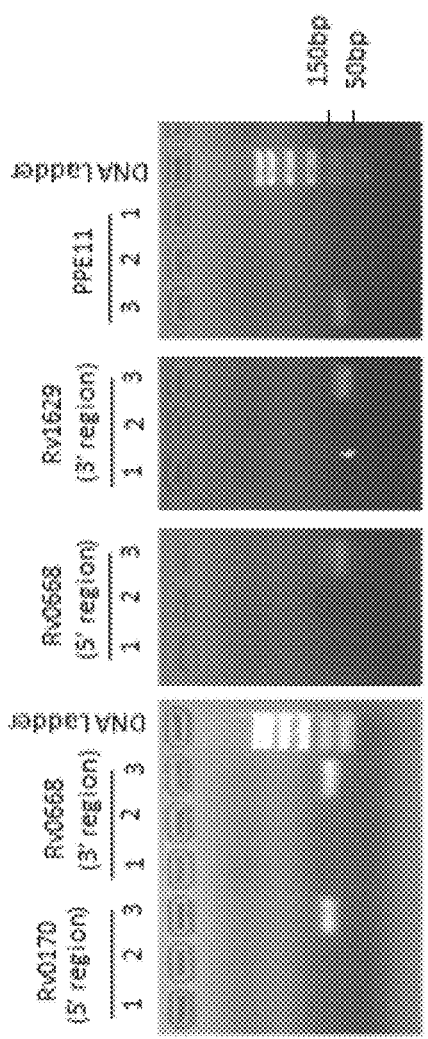
FIG. 9 illustrates the presence of Mtb transcripts in exosomes isolated from infected mice. Exosomes were isolated from the serum of Mtb-infected and uninfected mice. 10 pico-grams of exosomal RNA was used for RT-PCR with gene-specific primers. For some genes, primer pairs corresponding to the 5' and 3' ends of the transcript were tested. Lane 1: no template control; Lane 2 and 3: exosomal RNA from uninfected and H37Rv infected mice, respectively.

In order to determine if mycobacterial transcripts were restricted to in vitro-infected macrophages, we retro-orbitally infected C57BL/6 mice with $10^6$ H37Rv Mtb and isolated serum 15 days post-infection. Exosomes were purified from the serum by filtration and differential centrifugation. We obtained approximately 5 ng of exosomal RNA from each mouse. Serum exosomes were isolated from Mtb-infected C57BL/6 mice. Sequencing of the exosomal RNA resulted in the identification of several potential Mtb transcripts of which a subset was selected for validation by RT-PCR. As shown in FIG. 9, exosomal RNA from Mtb-infected cells (but not from uninfected cells) yielded PCR products corresponding to the correct size of the target gene.

Figure 10:
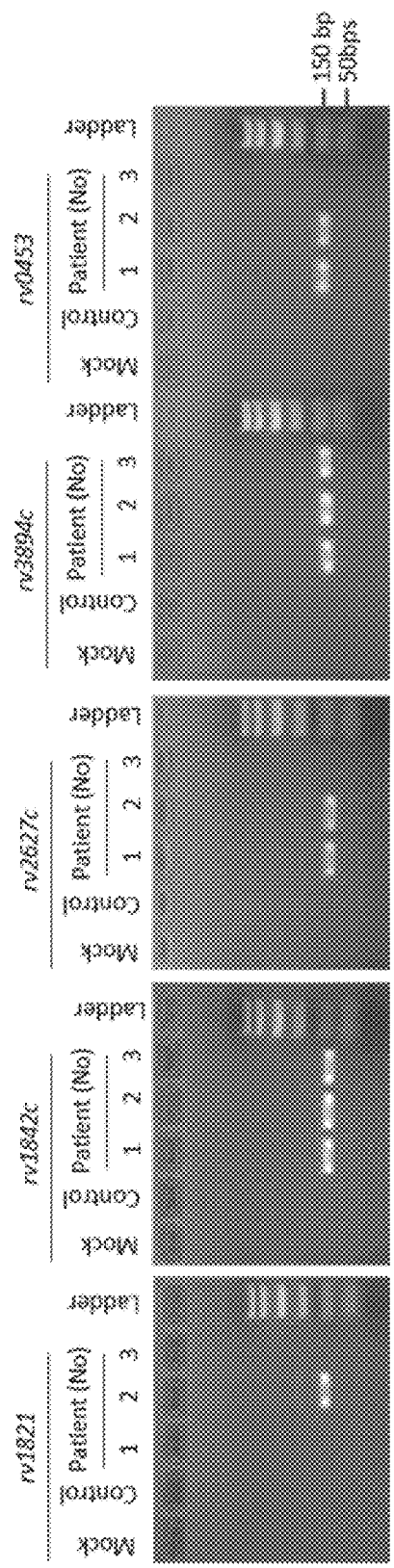
FIG. 10 illustrates Mtb transcripts detected in exosomes from TB patient serum. Exosomes were isolated from the serum of three TB patients and one healthy control. Isolated exosomal RNA was subject to RT-PCR using Mtb specific primers to amplify ~100 bp fragments. Mock, no DNA template; Control, healthy donor.

To further determine if exosomes isolated from TB patient sera also contain Mtb transcripts, we isolated exosomes from the 1.0 ml of serum from 3 TB patients and from one control uninfected individual. The serum was generously provided through a collaboration with the Foundation for New and Innovative Diagnostics (FIND). Exosomes were treated with RNase and DNAase to remove any surface bound nucleic acids, lysed, and RNA was isolated for sequencing. The cDNA library was prepared by NEBNext Ultra RNA Library Prep Kit and the sequencing performed using an Illumina NextSeq system. Sequence analysis of the exosomal RNA from TB patients identified 11 potential Mtb transcripts. To confirm the sequencing results 10 picograms of isolated exosomal RNA was used for RT-PCR using primers that would amplify fragments of specific Mtb transcripts. Four of the amplified transcripts are shown below. Analogous to our sequencing results, we identified some Mtb transcripts in all 3 patients while others were only observed in 1 or 2 patients (FIG. 10).

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A method for identifying an active *M. tuberculosis* infection in a subject comprising:

isolating extracellular vesicles from bodily fluid of a subject, wherein the extracellular vesicles contain a plurality of RNA;

extracting at least a portion of the RNA from the extracellular vesicle; and analyzing the RNA for the presence of one or more RNA that are indicative of an active *M. tuberculosis* infection; wherein the RNA that are indicative of an active

*M. tuberculosis* infection are selected from the group consisting of 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759 and 713, thereby determining the presence or absence of an active *M. tuberculosis* infection in the subject.

2. The method of claim 1, further comprising providing a means for detecting the at least one RNA.

3. The method of claim 2, wherein the means for detecting is a capture probe.

4. The method of claim 3, wherein the capture probe comprises a nucleotide sequence at least partially complementary to RNA sought to be detected.

5. The method of claim 1, wherein analyzing the RNA comprises creating cDNA from the plurality of RNA.

6. The method of claim 5, further comprising quantitating a level of one or more of the extracted RNA using qRT-PCR.

7. The method of claim 1, wherein the bodily fluid comprises blood, blood serum, blood plasma or urine.

8. The method of claim 1, further comprising comparing an RNA expression profile of the RNA extracted from the subject with a second RNA expression profile from a control subject.

9. The method of claim 1, wherein the extracellular vesicles are concentrated prior to extracting the RNA.

10. The method of claim 1, wherein the extracellular vesicles are exosomes.

11. The method of claim 1, wherein the RNA that are indicative of an active *M. tuberculosis* infection further comprise at least one of RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, RV2796, and RV2024c.

12. The method of claim 11, wherein the RNA indicative of an active *M. tuberculosis* infection comprise RV0740, RV0288, RV1344, RV0968, RV1942c, RV0664, RV0190, and RV1757c.

13. The method of claim 11, wherein the RNA indicative of an active *M. tuberculosis* infection comprise RV3809c, RV3533, RV2043, RV1101c, RV2024c, RV0740, RV0288, RV1344, RV0968, RV1942c, RV0664, RV0190, and RV1757c.

14. The method of claim 13, wherein the RNA indicative of an active *M. tuberculosis* infection comprise RV2796 and RV1369c, and wherein the RNA indicative of an active *M. tuberculosis* infection is isolated from exosomes taken from blood serum.

15. The method of claim 11, wherein the RNA that are indicative of an active *M. tuberculosis* infection are at least nine selected from the group consisting of RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, RV2796, and RV2024c.

16. The method of claim 1, wherein the RNA that are indicative of an active *M. tuberculosis* infection are at least nine selected from the group consisting of 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759 and 713.

17. A method for identifying an active *M. tuberculosis* infection in a subject comprising:
isolating extracellular vesicles from bodily fluid of a subject, wherein the extracellular vesicles contain a plurality of RNA;
extracting at least a portion of the RNA from the extracellular vesicle; and
analyzing the RNA for the presence of one or more RNA that are indicative of an active *M. tuberculosis* infection, wherein the RNA indicative of an active *M. tuberculosis* infection is at least a portion of an mRNA transcript of lipocalin-2;
thereby determining the presence or absence of an active *M. tuberculosis* infection in the subject.

18. A method for identifying an active *M. tuberculosis* infection in a subject comprising:
isolating extracellular vesicles from bodily fluid of a subject, wherein the extracellular vesicles contain a plurality of RNA;
extracting at least a portion of the RNA from the extracellular vesicle; and
analyzing the RNA for the presence of one or more RNA that are indicative of an active *M. tuberculosis* infection;
wherein the RNA indicative of an active *M. tuberculosis* infection are selected from the group consisting of RV1821, RV1842c, RV3894c, RV0453, RV1629, RV0170, RV0668, RV0740, RV0288, RV1344, RV0968, RV1942c, RV0664, RV0190, RV1757c, RV1369c, and RV2796, and comprise RV3809c, RV3533, RV0243, RC1101c, and RV2024c;
thereby determining the presence or absence of an active *M. tuberculosis* infection in the subject.

19. A method for identifying an active *M. tuberculosis* infection in a subject comprising:
isolating extracellular vesicles from bodily fluid of a subject, wherein the extracellular vesicles contain a plurality of RNA;
extracting at least a portion of the RNA from the extracellular vesicle; and
analyzing the RNA for the presence of one or more RNA that are indicative of an active *M. tuberculosis* infection;
wherein the RNA that are indicative of an active *M. tuberculosis* infection are selected from the group consisting of RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, RV2796, RV2024c, 149-3p, 181c-5p, 1839-3p, 151-3p, 214-3p, 292-3p, 3107-5p, 3074-5p, 344i, 486-5p, 486-3p, 434-5p, 598-3p, 5099, 5113, 5106, 5097, 5621-5p, 5115, 5111-5p, 714, 877-3p, 759 and 713, and wherein the RNA indicative of an active *M. tuberculosis* infection is at least a portion of an mRNA transcript of lipocalin-2;
thereby determining the presence or absence of an active *M. tuberculosis* infection in the subject.

20. A method for identifying an active *M. tuberculosis* infection in a subject comprising:
isolating exosomes from blood serum of a subject, wherein the exosomes contain a plurality of RNA;
extracting at least a portion of the RNA from the exosomes; and
analyzing the RNA for the presence of a group of RNA that are indicative of an active *M. tuberculosis* infection,
wherein the group of RNA that are indicative of an active *M. tuberculosis* infection comprise each of RV1821, RV1842c, RV3894c, RV0453, RV1629, RV0170, RV0668, RV0740, RV0288, RV1344, RV0968, RV1942c, RV0664, RV0190, RV1757c, RV1369c, RV3809c, RV3533, RV0243, RV1101c, RV2796, and RV2024c;
thereby determining the presence or absence of an active *M. tuberculosis* infection in the subject.

* * * * *

UNITED STATES PATENT AND TRADEMARK OFFICE
CERTIFICATE OF CORRECTION

| | |
|---|---|
| PATENT NO. | : 10,526,665 B2 |
| APPLICATION NO. | : 15/449324 |
| DATED | : January 7, 2020 |
| INVENTOR(S) | : Jeffrey S. Schorey et al. |

It is certified that error appears in the above-identified patent and that said Letters Patent is hereby corrected as shown below:

In the Specification

At Column 1, Line 13, please delete "RO1 AIO52439-06" and insert -- R01 AI052439 -- therefor.

Signed and Sealed this
Fifth Day of July, 2022

*Katherine Kelly Vidal*

Katherine Kelly Vidal
*Director of the United States Patent and Trademark Office*